United States Patent
Morita

(10) Patent No.: US 9,826,884 B2
(45) Date of Patent: Nov. 28, 2017

(54) IMAGE PROCESSING DEVICE FOR CORRECTING CAPTURED IMAGE BASED ON EXTRACTED IRREGULARITY INFORMATION AND ENHANCEMENT LEVEL, INFORMATION STORAGE DEVICE, AND IMAGE PROCESSING METHOD

(71) Applicant: OLYMPUS CORPORATION, Tokyo (JP)

(72) Inventor: Yasunori Morita, Hachioji (JP)

(73) Assignee: OLYMPUS COPORATION, Tokyo (JP)

( * ) Notice: Subject to any disclaimer, the term of this patent is extended or adjusted under 35 U.S.C. 154(b) by 144 days.

(21) Appl. No.: 14/727,213

(22) Filed: Jun. 1, 2015

(65) Prior Publication Data
US 2015/0257628 A1 Sep. 17, 2015

Related U.S. Application Data

(63) Continuation of application No. PCT/JP2013/072789, filed on Aug. 27, 2013.

(30) Foreign Application Priority Data

Dec. 25, 2012 (JP) ................................. 2012-281030

(51) Int. Cl.
*G06K 9/00* (2006.01)
*A61B 1/00* (2006.01)
(Continued)

(52) U.S. Cl.
CPC ...... *A61B 1/00004* (2013.01); *A61B 1/00009* (2013.01); *A61B 1/00059* (2013.01);
(Continued)

(58) Field of Classification Search
CPC ............ A61B 1/00004; A61B 1/00009; A61B 1/00059; A61B 1/04; G01B 11/14;
(Continued)

(56) References Cited

U.S. PATENT DOCUMENTS

| | | | |
|---|---|---|---|
| 2009/0074269 A1* | 3/2009 | Nishimura | A61B 1/04 382/128 |
| 2009/0074270 A1* | 3/2009 | Tanaka | G06K 9/4609 382/128 |
| 2009/0322863 A1 | 12/2009 | Takahashi | |

FOREIGN PATENT DOCUMENTS

| | | |
|---|---|---|
| JP | H01-185240 A | 7/1989 |
| JP | 2003-088498 A | 3/2003 |

(Continued)

OTHER PUBLICATIONS

International Search Report dated Oct. 1, 2013 issued in PCT/JP2013/072789.

*Primary Examiner* — Nirav G Patel
(74) *Attorney, Agent, or Firm* — Scully, Scott, Murphy & Presser, P.C.

(57) ABSTRACT

An image processing device includes an image acquisition section that acquires a captured image that includes an image of an object, the captured image being an image captured by an imaging section, a distance information acquisition section that acquires distance information based on the distance from the imaging section to the object when the imaging section captured the captured image, an irregularity information acquisition section that acquires extracted irregularity information from the acquired distance information, the extracted irregularity information being information that represents irregular parts extracted from the object, and an enhancement section that performs an enhancement process on an enhancement target, the enhancement target being an irregular part that is represented by the extracted (Continued)

irregularity information and agrees with characteristics specified by known characteristic information, the known characteristic information being information that represents known characteristics relating to the structure of the object.

12 Claims, 21 Drawing Sheets

(51) Int. Cl.
    *A61B 1/04*      (2006.01)
    *G01C 3/06*      (2006.01)
    *G01B 11/24*      (2006.01)
    *G02B 23/24*      (2006.01)
    *G01B 11/14*      (2006.01)

(52) U.S. Cl.
    CPC ................ *A61B 1/04* (2013.01); *G01B 11/14* (2013.01); *G01B 11/24* (2013.01); *G01C 3/06* (2013.01); *G02B 23/24* (2013.01); *G02B 23/2415* (2013.01)

(58) Field of Classification Search
    CPC .......... G01B 11/24; G01C 3/06; G02B 23/24; G02B 23/2415
    See application file for complete search history.

(56) References Cited

FOREIGN PATENT DOCUMENTS

| | | |
|---|---|---|
| JP | 2008-023266 A | 2/2008 |
| JP | 2010-005095 A | 1/2010 |
| JP | 2012-143363 A | 8/2012 |
| JP | 2013-013481 A | 1/2013 |

\* cited by examiner

SURFACE OF TISSUE   DISTANCE

CLOSING PROCESS

DETECTION OF RECESSES

OPENING PROCESS

DETECTION OF PROTRUSIONS

FIG. 6F   CHANGE DIAMETER (RADIUS) OF
SPHERE CORRESPONDING TO DISTANCE

PART OF DISTANCE MAP
OBJECT IS CAPTURED MORE DARKLY AS DISTANCE INCREASES,
AND CAPTURED MORE BRIGHTLY AS DISTANCE DECREASES

PART OF DISTANCE MAP
OBJECT IS CAPTURED MORE DARKLY AS DISTANCE INCREASES,
AND CAPTURED MORE BRIGHTLY AS DISTANCE DECREASES

IMAGE PROCESSING DEVICE FOR CORRECTING CAPTURED IMAGE BASED ON EXTRACTED IRREGULARITY INFORMATION AND ENHANCEMENT LEVEL, INFORMATION STORAGE DEVICE, AND IMAGE PROCESSING METHOD

CROSS REFERENCE TO RELATED APPLICATION

This application is a continuation of International Patent Application No. PCT/JP 2013/072789, having an international filing date of Aug. 27, 2013, which designated the United States, the entirety of which is incorporated herein by reference. Japanese Patent Application No. 2012-281030 filed on Dec. 25, 2012 is also incorporated herein by reference in its entirety.

BACKGROUND

The present invention relates to an image processing device, an information storage device, an image processing method, and the like.

When observing tissue using an endoscope apparatus, and making a diagnosis, a method has been widely used that determines whether or not an early lesion has occurred by observing the surface of tissue as to the presence or absence of minute irregularities (irregular parts). When using an industrial endoscope apparatus instead of a medical endoscope apparatus, it is useful to observe the object (i.e., the surface of the object in a narrow sense) as to the presence or absence of an irregular structure in order to detect whether or not a crack has occurred in the inner side of a pipe that is difficult to directly observe with the naked eye, for example. It is normally useful to detect the presence or absence of an irregular structure from the processing target image (object) when using an image processing device other than an endoscope apparatus.

A process that enhances a specific spatial frequency has been widely used as a process for enhancing a structure (e.g., an irregular structure such as a groove) within the captured image. However, this method is not suitable for detecting the presence or absence of minute irregularities (see above). A method has also been known that effects some change in the object, and captures the object, instead of detecting the presence or absence of irregularities by image processing. For example, when using a medical endoscope apparatus, the contrast of the mucous membrane in the surface area may be increased by spraying a dye (e.g., indigocarmine) to stain the tissue. However, it takes time and cost to spray a dye, and the original color of the object, or the visibility of a structure other than irregularities, may be impaired due to the sprayed dye. Moreover, the method that sprays a dye to tissue may be highly invasive for the patient.

JP-A-2003-88498 discloses a method that enhances an irregular structure by comparing the luminance level of an attention pixel in a locally extracted area with the luminance level of its peripheral pixel, and coloring the attention area when the attention area is darker than the peripheral area.

The process disclosed in JP-A-2003-88498 is designed based on the assumption that the object (i.e., the surface of tissue) is captured darkly when the distance from the imaging section to the object is long, since the intensity of reflected light from the surface of the tissue decreases.

SUMMARY

According to one aspect of the invention, there is provided an image processing device comprising:

an image acquisition section that acquires a captured image that includes an image of an object, the captured image being an image captured by an imaging section;

a distance information acquisition section that acquires distance information based on a distance from the imaging section to the object when the imaging section captured the captured image;

an irregularity information acquisition section that acquires extracted irregularity information from the acquired distance information, the extracted irregularity information being information that represents irregular parts extracted from the object; and an enhancement section that performs an enhancement process on an enhancement target, the enhancement target being an irregular part among the irregular parts represented by the extracted irregularity information that agrees with characteristics specified by known characteristic information, the known characteristic information being information that represents known characteristics relating to a structure of the object.

According to another aspect of the invention, there is provided an information storage device storing a program that causes a computer to perform steps of:

acquiring a captured image that includes an image of an object, the captured image being an image captured by an imaging section;

acquiring distance information based on a distance from the imaging section to the object when the imaging section captured the captured image;

acquiring extracted irregularity information from the acquired distance information, the extracted irregularity information being information that represents irregular parts extracted from the object; and performing an enhancement process on an enhancement target, the enhancement target being an irregular part among the irregular parts represented by the extracted irregularity information that agrees with characteristics specified by known characteristic information, the known characteristic information being information that represents known characteristics relating to a structure of the object.

According to another aspect of the invention, there is provided an image processing method comprising:

acquiring a captured image that includes an image of an object, the captured image being an image captured by an imaging section;

acquiring distance information based on a distance from the imaging section to the object when the imaging section captured the captured image;

acquiring extracted irregularity information from the acquired distance information, the extracted irregularity information being information that represents irregular parts extracted from the object; and performing an enhancement process on an enhancement target, the enhancement target being an irregular part among the irregular parts represented by the extracted irregularity information that agrees with characteristics specified by known characteristic information, the known characteristic information being information that represents known characteristics relating to a structure of the object.

BRIEF DESCRIPTION OF THE DRAWINGS

FIGS. 6A to 6F are views illustrating an extracted irregularity information extraction process using a morphological process.

Figure 1:
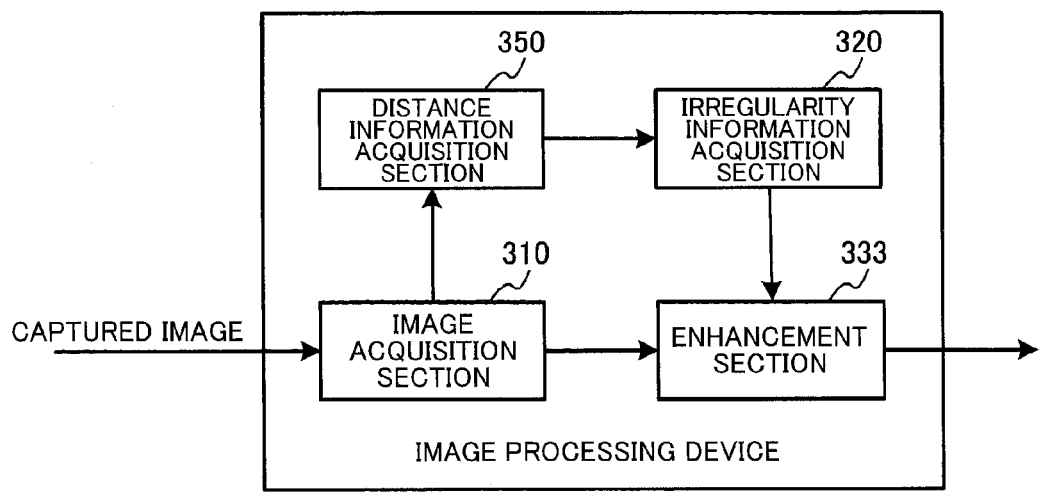
FIG. 1 illustrates a system configuration example of an image processing device.

DESCRIPTION OF EXEMPLARY
EMBODIMENTS

According to one embodiment of the invention, an image processing device includes:

an image acquisition section that acquires a captured image that includes an image of an object, the captured image being an image captured by an imaging section;

a distance information acquisition section that acquires distance information based on a distance from the imaging section to the object when the imaging section captured the captured image;

an irregularity information acquisition section that acquires extracted irregularity information from the acquired distance information, the extracted irregularity information being information that represents irregular parts extracted from the object; and an enhancement section that performs an enhancement process on an enhancement target, the enhancement target being an irregular part among the irregular parts represented by the extracted irregularity information that agrees with characteristics specified by known characteristic information, the known characteristic information being information that represents known characteristics relating to a structure of the object.

According to another embodiment of the invention, an information storage device storing a program causes a computer to perform steps of:

acquiring a captured image that includes an image of an object, the captured image being an image captured by an imaging section;

acquiring distance information based on a distance from the imaging section to the object when the imaging section captured the captured image;

acquiring extracted irregularity information from the acquired distance information, the extracted irregularity information being information that represents irregular parts extracted from the object; and performing an enhancement process on an enhancement target, the enhancement target being an irregular part among the irregular parts represented by the extracted irregularity information that agrees with characteristics specified by known characteristic information, the known characteristic information being information that represents known characteristics relating to a structure of the object.

According to another embodiment of the invention, an image processing method includes:

acquiring a captured image that includes an image of an object, the captured image being an image captured by an imaging section;

acquiring distance information based on a distance from the imaging section to the object when the imaging section captured the captured image;

acquiring extracted irregularity information from the acquired distance information, the extracted irregularity information being information that represents irregular parts extracted from the object; and performing an enhancement process on an enhancement target, the enhancement target being an irregular part among the irregular parts represented by the extracted irregularity information that agrees with characteristics specified by known characteristic information, the known characteristic information being information that represents known characteristics relating to a structure of the object.

Exemplary embodiments of the invention are described below. Note that the following exemplary embodiments do not in any way limit the scope of the invention laid out in the claims. Note also that all of the elements described in connection with the following exemplary embodiments should not necessarily be taken as essential elements of the invention.

1. Method

As illustrated in FIG. 1, an image processing device according to several embodiments of the invention includes an image acquisition section 310 that acquires a captured image that includes an image of an object, the captured image being an image captured by an imaging section (e.g., imaging section 200 illustrated in FIG. 2 (described later)), a distance information acquisition section 350 that acquires distance information based on the distance from the imaging section to the object when the imaging section captured the captured image, an irregularity information acquisition section 320 that acquires extracted irregularity information from the acquired distance information, the extracted irregularity information being information that represents irregular parts extracted from the object, and an enhancement section 333 that performs an enhancement process on an enhancement target, the enhancement target being an irregular part among the irregular parts represented by the extracted irregularity information that agrees with characteristics specified by known characteristic information, the known characteristic information being information that represents known characteristics relating to the structure of the object.

Figure 6A:
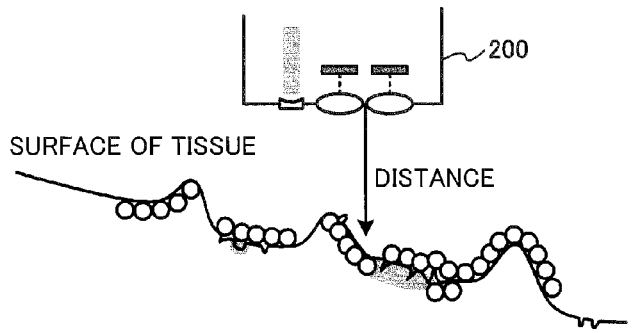

Since the distance information is information that corresponds to the distance from the imaging section 200 to the object, the distance information represents the structure of the object (i.e., tissue (particularly the surface of tissue) when using a medical endoscope apparatus) (see FIG. 6A). Specifically, the distance information includes information about a minute irregular structure present on the surface of the object.

However, the distance information also includes information about a structure other than the minute irregular structure that is present on the surface of the object. For example, a lumen structure (hollow tubular structure) (e.g., gullet or large intestine) is normally observed using an endoscope apparatus. In this case, since the wall surface of the structure (tissue) forms a curved surface having a given curvature, the distance represented by the distance information varies corresponding to the curved surface. In the example illustrated in FIG. 6A, the distance information includes information about various structures, but represents a structure as a whole in which the distance from the imaging section to the object increases in the rightward direction.

The surface of the object may also include an irregular structure that differs from the irregular structure that corresponds to the extracted irregularity information that is output using the method according to several embodiments of the invention. For example, a fold structure (see 2, 3, and 4 in FIG. 2) may be observed on the surface of the stomach, the large intestine, or the like. The distance information also includes information about such a fold structure. Note that several embodiments of the invention are intended to observe (using an endoscope apparatus) a minute irregular structure that differs in dimensions from such a structure that is normally observed on the surface of tissue.

Therefore, it is necessary to appropriately specify the information about the desired irregular structure from the distance information that includes a change in distance due to various structures in order to appropriately perform the enhancement process on the attention target. This also applies to the case of using an industrial endoscope apparatus. When using an industrial endoscope apparatus, the distance information may include a change in distance that corresponds to the curved surface of a circular pipe, information about a groove that is formed in advance in order to provide a pipe with a given function, information about a scratch or the like that may be missed due to low severity, and the like. In this case, such information is excluded from the distance information.

Several embodiments of the invention propose a method that acquires the known characteristic information (prior information) that is information that represents the known characteristics relating to the structure of the object, and enhances the irregular part of the object that agrees with the characteristics specified by the known characteristic information. The term "known characteristic information" used herein refers to information that makes it possible to classify the structures of the surface of the object into a useful structure and a structure that is not useful. Specifically, the known characteristic information may be information about an irregular part for which the enhancement process is useful (e.g., an irregular part that is useful for finding an early lesion). In this case, an object that agrees with the known characteristic information is determined to be the enhancement target. Alternatively, the known characteristic information may be information about a structure for which the enhancement process is not useful. In this case, an object that does not agree with the known characteristic information is determined to be the enhancement target. Alternatively, information about a useful irregular part and information about a structure that is not useful may be stored, and the range of the useful irregular part may be set with high accuracy.

Figure 11:
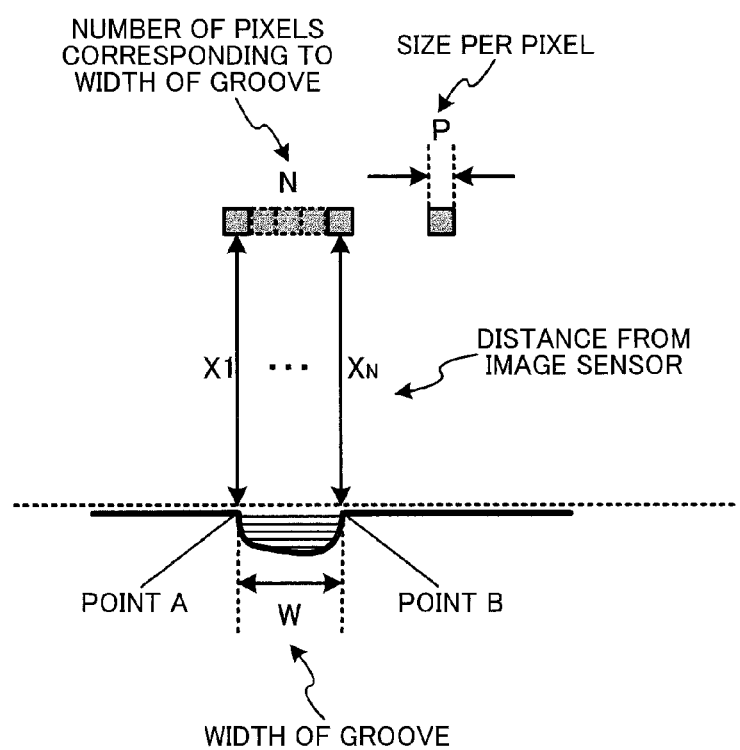
FIG. 11 is a view illustrating a recess width calculation process.

In several embodiments of the invention, dimensional information about the irregular part of the object is acquired using the method described later with reference to FIG. 11 and the like, and compared with the known characteristic information. In this case, it is necessary to set the reference plane (e.g., a plane that corresponds to x1 in FIG. 11) of the object in order to accurately calculate the dimensional information, and it is desirable to exclude a global change in distance (i.e., a change in distance due to a lumen structure in a narrow sense) from the distance information.

Therefore, several embodiments of the invention utilize a method that acquires the extracted irregularity information by extracting information about a specific structure from the distance information, and determines the enhancement target or the like from the extracted irregularity information and the known characteristic information. The extracted irregularity information in a narrow sense refers to information that excludes information about a lumen structure. In this case, information about a lumen structure may be acquired as the known characteristic information. Note that information about another structure (e.g., fold structure) that is not subjected to the enhancement process may also be excluded. It is possible to reduce the processing load when setting the enhancement target by excluding information about the structure of the object that is not subjected to the enhancement process as much as possible, for example. This process can be implemented by utilizing the known characteristic information that makes it possible to specify the enhancement target.

Note that the structure represented by (included in) the extracted irregularity information need not necessarily be strictly limited to the enhancement target structure. This is because the enhancement process used in connection with several embodiments of the invention is designed to use the known characteristic information that makes it possible to specify the enhancement target for the following three reasons. First, it is possible to improve the enhancement target selection accuracy by utilizing the known characteristic information during the enhancement process, even if the known characteristic information is used to acquire the extracted irregularity information. Second, the width of the irregular part is taken into account (as described later with reference to FIGS. 6A to 6F and the like) when acquiring the extracted irregularity information, and the depth and the height of the irregular part are not taken into account. Specifically, it is necessary to perform a process that utilizes the known characteristic information in addition to the process that acquires the extracted irregularity information when using the depth or the height of the irregular part. Third, the enhancement process may be implemented using a method that changes the enhancement level corresponding to the dimensional information or the like. Specifically, even if information that represents only the enhancement target can be acquired as the extracted irregularity information by performing an extraction process that utilizes the known characteristic information, the known characteristic information is required when setting the enhancement level.

Therefore, it suffices to perform only a process that makes it possible to appropriately perform the enhancement process (i.e., a process that excludes a global structure so that the reference plane can be set in a narrow sense) when extracting the extracted irregularity information, and an additional process is not indispensable. The known characteristic information may not be used when excluding information about a global structure as long as it is possible to appropriately set the reference plane.

It is considered that the known characteristic information (e.g., a typical fold size, or the dimensions of a useful irregular structure) that is used for the enhancement process (and optionally the extracted irregularity information extraction process) differs corresponding to the observation target part (e.g., stomach (upper digestive system) or large intestine (lower digestive system)). Therefore, it is desirable to provide the known characteristic information so that the known characteristic information can be selected or changed corresponding to the observation target, for example.

A first embodiment, a second embodiment, and a third embodiment of the invention are described below. Although the first embodiment, the second embodiment, and the third embodiment are described taking an endoscope apparatus (see FIG. 2) as an example, the first embodiment, the second embodiment, and the third embodiment can be applied to an image processing device (see FIG. 1) that is not limited to an endoscope apparatus.

The first embodiment illustrates a method that enhances a recess (groove) of the object. The second embodiment illustrates a method that enhances a protrusion (e.g., a polyp when using a medical endoscope apparatus) of the object. In the first embodiment and the second embodiment, a color conversion process is used as a specific example of the enhancement process. The third embodiment illustrates an enhancement method that increases contrast.

2. First Embodiment

The first embodiment is described below. A system configuration example of the endoscope apparatus that includes the image processing device according to the first embodiment will be described first, and the extracted irregularity information acquisition process, the enhancement process, and the distance information acquisition process will then be described. An example that implements the method according to the first embodiment by means of software will then be described, and the flow of the process according to the first embodiment will be described thereafter using a flowchart.

2.1 System Configuration Example

Figure 2:
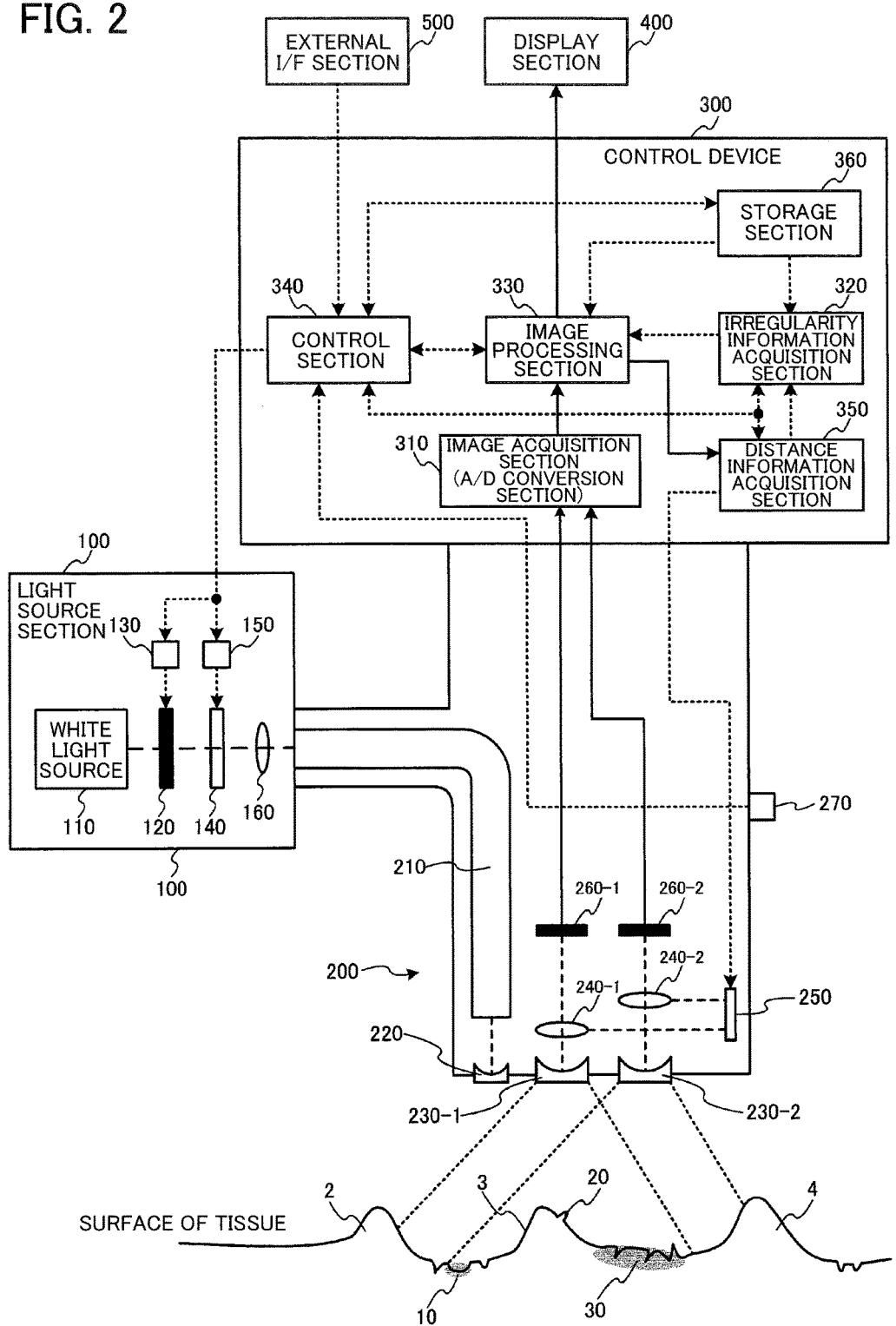
FIG. 2 illustrates a configuration example of an endoscope apparatus that includes an image processing device according to one embodiment of the invention.

FIG. 2 illustrates a configuration example of the endoscope apparatus according to the first embodiment. The endoscope apparatus includes a light source section 100, an imaging section 200, a control device 300 (processor section), a display section 400, and an external I/F section 500.

The light source section 100 includes a white light source 110, a light source aperture 120, a light source aperture driver section 130 that drives the light source aperture 120, and a rotary color filter 140 that includes a plurality of filters that differ in spectral transmittance. The light source section 100 also includes a rotation driver section 150 that drives the rotary color filter 140, and a condenser lens 160 that focuses light that has passed through the rotary color filter 140 on the incident end face of a light guide fiber 210. The light source aperture driver section 130 adjusts the intensity of light by opening and closing the light source aperture 120 based on a control signal output from a control section 340 included in the control device 300.

Figure 3:
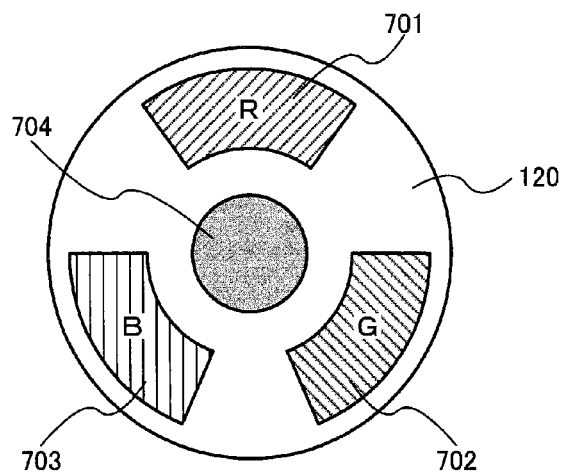
FIG. 3 illustrates a configuration example of a rotary color filter.

FIG. 3 illustrates a detailed configuration example of the rotary color filter 140. The rotary color filter 140 includes a red (R) color filter 701, a green (G) color filter 702, a blue (B) color filter 703, and a rotary motor 704.

Figure 4:
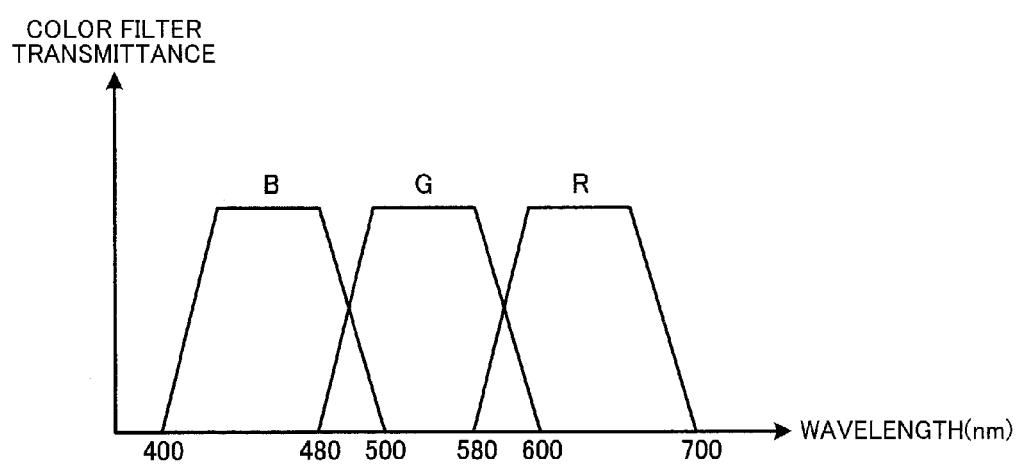
FIG. 4 illustrates an example of the spectral transmittance characteristics of a color filter.

FIG. 4 illustrates an example of the spectral characteristics of the color filters 701 to 703. The rotation driver section 150 rotates the rotary color filter 140 at a given rotational speed in synchronization with the imaging period of image sensors 260-1 and 260-2 based on the control signal output from the control section 340. For example, when the rotary color filter 140 is rotated at 20 revolutions per second, each color filter crosses the incident white light every 1/60th of a second. In this case, the image sensors 260-1 and 260-2 capture and transfer image signals every 1/60th of a second. The image sensors 260-1 and 260-2 are monochrome single-chip image sensors, for example. The image sensors 260-1 and 260-2 are implemented by a CCD image sensor or a CMOS image sensor, for example. Specifically, the endoscope apparatus according to the first embodiment frame-sequentially captures an R image, a G image, and a B image every 1/60th of a second.

The imaging section 200 is formed to be elongated and flexible so that the imaging section 200 can be inserted into a body cavity, for example. The imaging section 200 includes the light guide fiber 210 that guides the light focused by the light source section 100 to an illumination lens 220, and the illumination lens 220 that diffuses the light guided by the light guide fiber 210, and illuminates the observation object. The imaging section 200 further includes objective lenses 230-1 and 230-2 that focus the reflected light from the observation target, focus lenses 240-1 and 240-2 that adjust the focal distance, a lens driver section 250 that moves the positions of the focus lenses 240-1 and 240-2, and the image sensors 260-1 and 260-2 that detect the focused reflected light.

The objective lenses 230-1 and 230-2 are situated at a given interval so that a given parallax image (hereinafter may be referred to as "stereo image") can be captured. The objective lenses 230-1 and 230-2 respectively form a left image and a right image on the image sensors 260-1 and 260-2. The left image and the right image respectively output from the image sensors 260-1 and 260-2 are output to an image acquisition section (A/D conversion section) 310. Note that the distance information need not necessarily be acquired through a stereo matching process (described later with reference to FIG. 16). When acquiring the distance information using a method that does not utilize the parallax image, one objective lens, one focus lens, and one image sensor may be used (differing from the example illustrated in FIG. 2) instead of using a plurality of objective lenses, a plurality of focus lenses, and a plurality of image sensors.

The lens driver section 250 is a voice coil motor (VCM), for example, and is connected to the focus lenses 240-1 and 240-2. The lens driver section 250 adjusts the in-focus object plane position by switching the positions of the focus lenses 240-1 and 240-2 between consecutive positions. The imaging section 200 is provided with a switch 270 that allows the user to issue an enhancement process ON/OFF instruction. When the user has operated the switch 270, an enhancement process ON/OFF instruction signal is output from the switch 270 to the control section 340.

The control device 300 controls each section of the endoscope apparatus, and performs image processing. The control device 300 includes the image acquisition section (A/D conversion section) 310, an irregularity information acquisition section 320, an image processing section 330, the control section 340, a distance information acquisition section 350, and a storage section 360. The details of the irregularity information acquisition section 320 and the image processing section 330 are described later.

The image acquisition section (A/D conversion section) 310 converts the image signals into digital signals, and transmits the converted image signals to the image processing section 330. The image processing section 330 processes the image signals (digital signals), and transmits the image signals to the display section 400. The control section 340 controls each section of the endoscope apparatus. More specifically, the control section 340 synchronizes the light source aperture driver section 130, a lens position control section 359 (when the distance information acquisition section 350 has the configuration illustrated in FIG. 16), and the image processing section 330. The control section 340 is connected to the switch 270 and the external I/F section 500, and transmits the enhancement process ON/OFF instruction signal to the image processing section 330.

The distance information acquisition section 350 calculates the object distance using the image signals transmitted from the image processing section 330 under control of the control section 340. In the first embodiment, the information about the object distance is calculated by the stereo matching process. The information about the object distance is transmitted to the image processing section 330. The details of the distance information acquisition section 350 are described later.

The storage section 360 stores various type of information used for the process performed by the control device 300. The function of the storage section 360 may be implemented by a memory (e.g., RAM), a hard disk drive (HDD), or the like. The storage section 360 stores the known characteristic information used for the enhancement process and the like, for example.

The display section 400 is a display device that can display a movie (moving image), and is implemented by a CRT, a liquid crystal monitor, or the like.

The external I/F section 500 is an interface that allows the user to input information to the endoscope apparatus, for example. The external I/F section 500 includes an enhancement process button (not illustrated in the drawings) that allows the user to issue the enhancement process ON/OFF instruction, and the user can issue the enhancement process ON/OFF instruction using the external I/F section 500. Note that the function of the enhancement process button is the same as that of the switch 270 provided to the imaging section 200. The external I/F section 500 outputs the enhancement process ON/OFF instruction signal to the control section 340. The external I/F section 500 includes a power switch (power ON/OFF switch), a mode (e.g., imaging mode) switch button, and the like.

2.2 Extracted Irregularity Information Acquisition Process

The irregularity information acquisition section 320 extracts the extracted irregularity information that represents an irregular part on the surface of tissue from the distance information (object distance) input from the distance information acquisition section 350. A method that sets an extraction process parameter based on the known characteristic information, and extracts the extracted irregularity information from the distance information using an extraction process that utilizes the extraction process parameter, is described below. Specifically, an irregular part having the desired dimensional characteristics (i.e., an irregular part having a width within the desired range in a narrow sense) is extracted as the extracted irregularity information using the known characteristic information. Since the three-dimensional structure of the object is reflected in the distance information, the distance information includes information about the desired irregular part, and information about a global structure that is larger than the desired irregular part, and corresponds to a fold structure, and the wall surface structure of a lumen. Specifically, the extracted irregularity information acquisition process may be referred to as a process that excludes information about a fold structure and a lumen structure from the distance information.

Note that the extracted irregularity information acquisition process is not limited thereto. For example, the extracted irregularity information acquisition process may not utilize the known characteristic information. When the extracted irregularity information acquisition process utilizes the known characteristic information, various types of information may be used as the known characteristic information. For example, the extraction process may exclude information about a lumen structure from the distance information, but allow information about a fold structure to remain. In such a case, it is also possible to perform the enhancement process on the desired object since the known characteristic information is used during the enhancement process described later.

Figure 5:
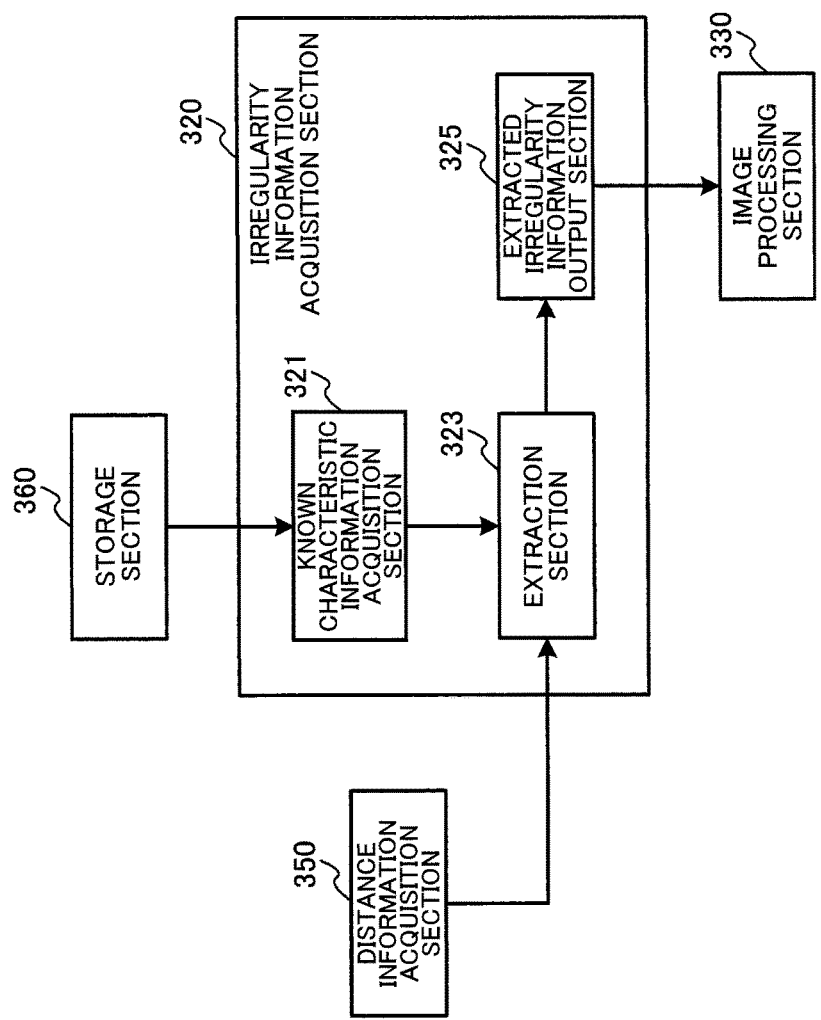
FIG. 5 illustrates a configuration example of an irregularity information acquisition section.

FIG. 5 illustrates a configuration example of the irregularity information acquisition section 320. The irregularity information acquisition section 320 includes a known characteristic information acquisition section 321, an extraction section 323, and an extracted irregularity information output section 325. Note that the configuration of the irregularity information acquisition section 320 is not limited to the configuration illustrated in FIG. 5. Various modifications may be made, such as omitting some of the elements illustrated in FIG. 5, or adding other elements.

The known characteristic information acquisition section 321 acquires the known characteristic information from the storage section 360. Specifically, the known characteristic information acquisition section 321 acquires the size (i.e., dimensional information (e.g., width, height, or depth)) of the extraction target irregular part of tissue due to a lesion, the size (i.e., dimensional information (e.g., width, height, or depth)) of the lumen and the folds of the observation target part based on observation target part information, and the like as the known characteristic information. Note that the observation target part information is information that represents the observation target part that is determined based on scope ID information, for example. The observation target part information may also be included in the known characteristic information. For example, when the scope is an upper gastrointestinal scope, the observation target part is the gullet, the stomach, or the duodenum. When the scope is a lower gastrointestinal scope, the observation target part is the large intestine. Since the dimensional information about the extraction target irregular part and the dimensional information about the lumen and the folds of the observation target part differ corresponding to each part, the known characteristic information acquisition section 321 outputs information about a typical size of a lumen and folds acquired based on the observation target part information to the extraction section 323, for example. Note that the observation target part information need not necessarily be determined based on the scope ID information. For example, the user may select the observation target part information using a switch provided to the external I/F section 500.

The extraction section 323 determines the extraction process parameter based on the known characteristic information, and performs the extracted irregularity information extraction process based on the determined extraction process parameter.

The extraction section 323 performs a low-pass filtering process using a given size (N×N pixels) on the input distance information to extract rough distance information. The extraction section 323 adaptively determines the extraction process parameter based on the extracted rough distance information. The details of the extraction process parameter are described later. The extraction process parameter may be the morphological kernel size (i.e., the size of a structural element) that is adapted to the distance information at the plane position orthogonal to the distance information of the distance map, a low-pass filter that is adapted to the distance information at the plane position, or a high-pass filter that is adapted to the plane position, for example. Specifically, the extraction process parameter is change information that changes an adaptive nonlinear or linear low-pass filter or high-pass filter corresponding to the distance information. Note that the low-pass filtering process is performed to suppress a decrease in the accuracy of the extraction process that may occur when the extraction process parameter changes frequently or significantly corresponding to the position within the image. The low-pass filtering process may not be performed when a decrease in the accuracy of the extraction process does not occur.

The extraction section 323 performs the extraction process based on the determined extraction process parameter to extract only the irregular parts of the object having the desired size. The extracted irregular parts are output to the image processing section 330 as the extracted irregularity information (irregularity image) having the same size as that of the captured image (i.e., the image subjected to the enhancement process).

The details of the extraction process parameter determination process performed by the extraction section 323 are described below with reference to FIGS. 6A to 6F. In FIGS. 6A to 6F, the extraction process parameter is the diameter of a structural element (sphere) used for an opening process and a closing process (morphological process). FIG. 6A is a view schematically illustrating the surface of the object (tissue) and the vertical cross section of the imaging section 200. The folds (2, 3, and 4 in FIG. 2) on the surface of the tissue are gastric folds, for example. As illustrated in FIG. 2, early lesions 10, 20, and 30 are formed on the surface of the tissue.

The extraction process parameter determination process performed by the extraction section 323 is intended to determine the extraction process parameter for extracting only an irregular part useful for specifying the early lesions 10, 20, and 30 from the surface of the tissue without extracting the folds 2, 3, and 4 from the surface of the tissue.

In order to determine such an extraction process parameter, it is necessary to use the size (i.e., dimensional information (e.g., width, height, or depth)) of the extraction target irregular part of tissue due to a lesion, and the size (i.e., dimensional information (e.g., width, height, or depth)) of the lumen and the folds of the observation target part based on the observation target part information (that are stored in the storage section 360).

It is possible to extract only the desired irregular part by determining the diameter of the sphere (with which the surface of the tissue is traced during the opening process and the closing process) using the above information. The diameter of the sphere is set to be smaller than the size of the lumen and the folds of the observation target part based on the observation target part information, and larger than the size of the extraction target irregular part of tissue due to a lesion. It is desirable to set the diameter of the sphere to be equal to or smaller than half of the size of the folds, and equal to or larger than the size of the extraction target irregular part of tissue due to a lesion. FIGS. 6A to 6F illustrate an example in which a sphere that satisfies the above conditions is used for the opening process and the closing process.

Figure 6B:
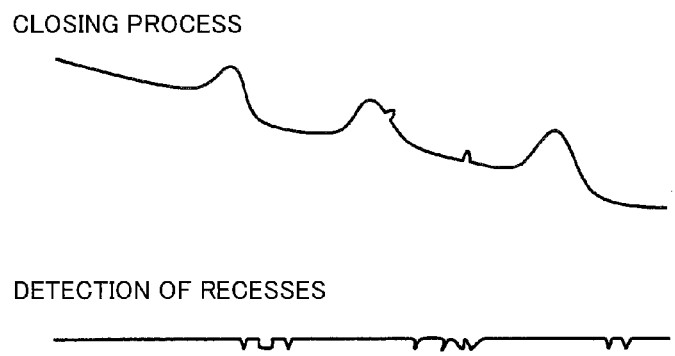
Figure 6C:
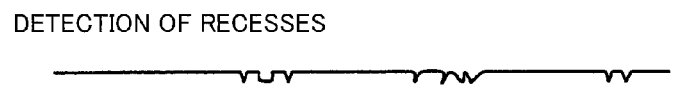

FIG. 6B illustrates the surface of the tissue after the closing process has been performed. As illustrated in FIG. 6B, information in which the recesses among the irregular parts having the extraction target dimensions are filled while maintaining the change in distance due to the wall surface of the tissue, and the structures such as the folds, is obtained by determining an appropriate extraction process parameter (i.e., the size of the structural element). Only the recesses on the surface of the tissue can be extracted (see FIG. 6C) by calculating the difference between information obtained by the closing process and the original surface of the tissue (see FIG. 6A).

Figure 6D:
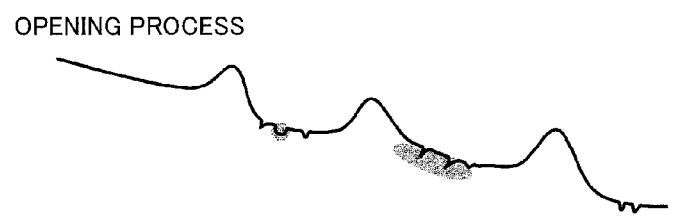
Figure 6E:
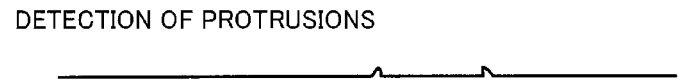
Figure 6E:
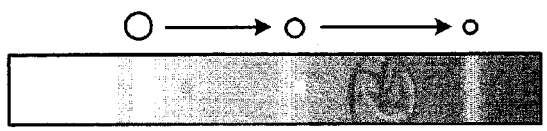

FIG. 6D illustrates the surface of the tissue after the opening process has been performed. As illustrated in FIG. 6D, information in which the protrusions among the irregular parts having the extraction target dimensions are removed, is obtained by the opening process. Only the protrusions on the surface of the tissue can be extracted (see FIG. 6E) by calculating the difference between information obtained by the opening process and the original surface of the tissue.

The opening process and the closing process may be performed on the surface of the tissue using a sphere having an identical size. However, since the stereo image is characterized in that the area of the image formed on the image sensor decreases as the distance represented by the distance information increases, the diameter of the sphere may be increased when the distance represented by the distance information is short, and may be decreased when the distance represented by the distance information is long in order to extract an irregular part having the desired size.

FIG. 6F illustrates an example in which the diameter of the sphere is changed with respect to the average distance information when performing the opening process and the closing process on the distance map. Specifically, it is necessary to correct the actual size of the surface of the tissue using the optical magnification to agree with the pixel pitch of the image formed on the image sensor in order to extract the desired irregular part with respect to the distance map. Therefore, it is desirable that the extraction section 323 acquire the optical magnification or the like of the imaging section 200 that is determined based on the scope ID information.

Specifically, the process that determines the size of the structural element (extraction process parameter) is performed so that the exclusion target shape (e.g., folds) is not deformed (i.e., the sphere moves to follow the exclusion target shape) when the process using the structural element is performed on the exclusion target shape (when the sphere is moved on the surface in FIG. 6A). The process that determines the size of the structural element (extraction process parameter) is performed so that the extraction target irregular part (extracted irregularity information) is removed (i.e., the sphere does not enter the recess or the protrusion) when the process using the structural element is performed on the extraction target irregular part. Since the morphological process is a well-known process, detailed description thereof is omitted.

The extraction process is not limited to the morphological process. The extraction process may be implemented using a filtering process. For example, when using a low-pass filtering process, the characteristics of the low-pass filter are determined so that the extraction target irregular part of tissue due to a lesion can be smoothed, and the structure of the lumen and the folds of the observation target part can be maintained. Since the characteristics of the extraction target (i.e., irregular part) and the exclusion target (i.e., folds and lumen) can be determined from the known characteristic information, the spatial frequency characteristics are known, and the characteristics of the low-pass filter can be determined.

The low-pass filter may be a known Gaussian filter or bilateral filter. The characteristics of the low-pass filter may be controlled using a parameter σ, and a σ map corresponding to each pixel of the distance map may be generated. When using a bilateral filter, the σ map may be generated using either or both of a luminance difference parameter σ and a distance parameter σ. A Gaussian filter is represented by the following expression (1), and a bilateral filter is represented by the following expression (2).

$$f(x) = \frac{1}{N}\exp\left(-\frac{(x-x0)^2}{2\sigma^2}\right) \quad (1)$$

$$f(x) = \frac{1}{N}\exp\left(-\frac{(x-x0)^2}{2\sigma_c^2}\right) \times \exp\left(-\frac{(p(x)-p(x0))^2}{2\sigma_v^2}\right) \quad (2)$$

For example, a σ map subjected to a thinning process may be generated, and the desired low-pass filter may be applied to the distance map using the σ map.

The parameter σ that determines the characteristics of the low-pass filter is set to be larger than a value obtained by multiplying the pixel-to-pixel distance D1 of the distance map corresponding to the size of the extraction target irregular part by α (>1), and smaller than a value obtained by multiplying the pixel-to-pixel distance D2 of the distance map corresponding to the size of the lumen and the folds specific to the observation target part by β (<1). For example, σ may calculated by σ=(α*D1+β*D2)/2*Rσ.

Steeper sharp-cut characteristics may be set as the characteristics of the low-pass filter. In this case, the filter characteristics are controlled using a cut-off frequency fc instead of the parameter σ. The cut-off frequency fc may be set so that a frequency F1 in the cycle D1 does not pass through, and a frequency F2 in the cycle D2 does pass through. For example, the cut-off frequency fc may be set to fc=(F1+F2)/2*Rf.

Note that Rσ is a function of the local average distance. The output value increases as the local average distance decreases, and decreases as the local average distance increases. Rf is a function that is designed so that the output value decreases as the local average distance decreases, and increases as the local average distance increases.

A recess image can be output by extracting only a negative area obtained by subtracting the low-pass filtering results from the distance map that is not subjected to the low-pass filtering process. A protrusion image can be output by extracting only a positive area obtained by subtracting the low-pass filtering results from the distance map that is not subjected to the low-pass filtering process.

Figure 7A:
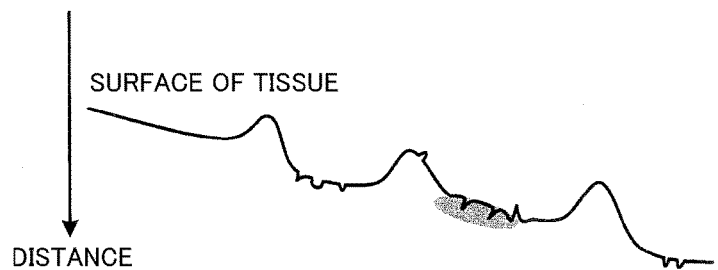
FIGS. 7A to 7D are views illustrating an extracted irregularity information extraction process using a filtering process.
Figure 7B:
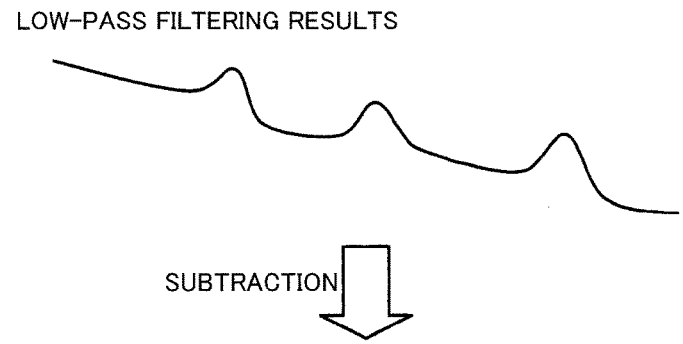
Figure 7C:
Figure 7D:
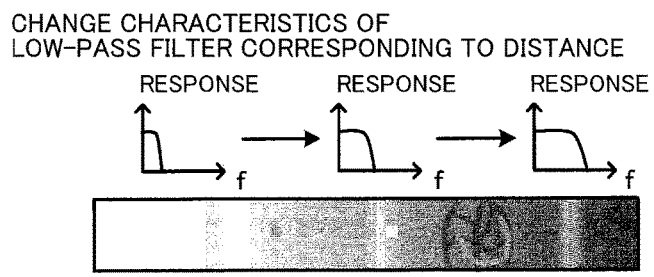

FIGS. 7A to 7D illustrate extraction of the desired irregular part due to a lesion using the low-pass filter. As illustrated in FIG. 7B, information in which the irregular parts having the extraction target dimensions are removed while maintaining the change in distance due to the wall surface of the tissue, and the structures such as the folds, is obtained by performing the filtering process using the low-pass filter on the distance map illustrated in FIG. 7A. Since the low-pass filtering results serve as a reference plane for extracting the desired irregular parts (see FIG. 7B) even if the opening process and the closing process (see FIGS. 6A to 6F) are not performed, the irregular parts can be extracted (see FIG. 7C) by performing a subtraction process on the original distance map (see FIG. 7A). When using the morphological process, the size of the structural element is adaptively changed corresponding to the rough distance information. When using the filtering process, it is desirable to change the characteristics of the low-pass filter corresponding to the rough distance information. FIG. 7D illustrates an example in which the characteristics of the low-pass filter are changed corresponding to the rough distance information.

A high-pass filtering process may be performed instead of the low-pass filtering process. In this case, the characteristics of the high-pass filter are determined so that the extraction target irregular part of tissue due to a lesion is maintained while removing the structure of the lumen and the folds specific to the observation target part.

The filter characteristics of the high-pass filter are controlled using a cut-off frequency fhc, for example. The cut-off frequency fhc may be set so that the frequency F1 in the cycle D1 passes through, and the frequency F2 in the cycle D2 does not pass through. For example, the cut-off frequency fhc may be set to fhc=(F1+F2)/2*Rf. Note that Rf is a function that is designed so that the output value decreases as the local average distance decreases, and increases as the local average distance increases.

The extraction target irregular part due to a lesion can be extracted directly by performing the high-pass filtering process. Specifically, the extracted irregularity information is acquired directly (see FIG. 7C) without performing a subtraction process (difference calculation process).

2.3 Enhancement Process

Figure 8:
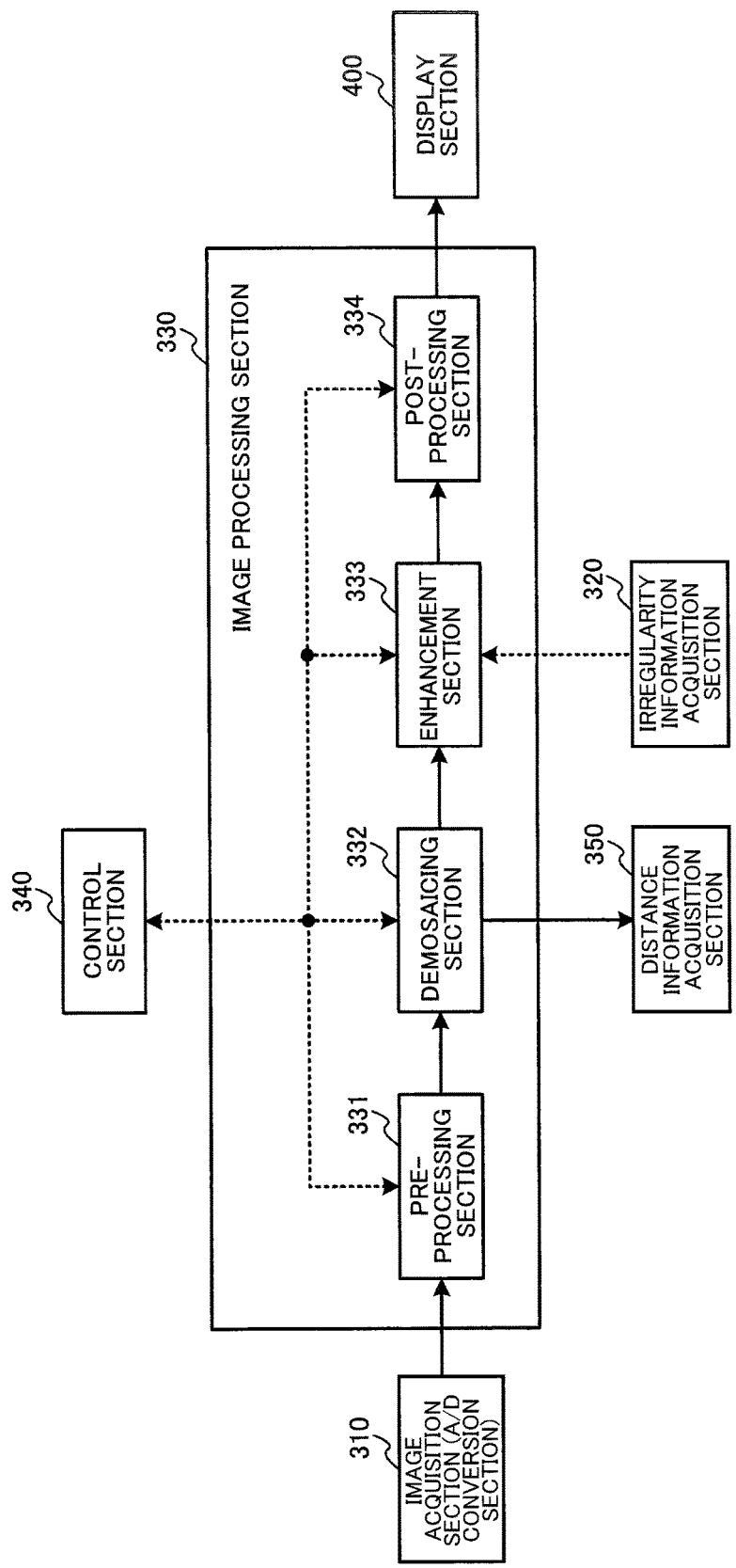
FIG. 8 illustrates a configuration example of an image processing section.

FIG. 8 illustrates a detailed configuration example of the image processing section 330 according to the first embodiment. The image processing section 330 includes a preprocessing section 331, a demosaicing section 332, an enhancement section 333, and a post-processing section 334. The image acquisition section (A/D conversion section) 310 is connected to the preprocessing section 331. The preprocessing section 331 is connected to the demosaicing section 332. The demosaicing section 332 is connected to the distance information acquisition section 350 and the enhancement section 333. The irregularity information acquisition section 320 is connected to the enhancement section 333. The enhancement section 333 is connected to the post-processing section 334. The post-processing section 334 is connected to the display section 400. The control section 340 is bidirectionally connected to each section, and controls each section.

The preprocessing section 331 performs an OB clamp process, a gain control process, and a WB correction process on the image signals input from the image acquisition section (A/D conversion section) 310 using an OB clamp value, a gain correction value, and a WB coefficient stored in the control section 340. The preprocessing section 331 transmits the resulting image signals to the demosaicing section 332.

The demosaicing section 332 performs a demosaicing process on the frame-sequential image signals processed by the preprocessing section 331 based on the control signal output from the control section 340. Specifically, the demosaicing section 332 stores the image signals that have been input frame sequentially and correspond to each color (light) (R, G, or B) on a frame basis, and simultaneously reads the stored image signals that correspond to each color (light). The demosaicing section 332 transmits the demosaiced image signals to the distance information acquisition section 350 and the enhancement section 333.

The enhancement section 333 performs an attention pixel enhancement process on the image signals transmitted from the demosaicing section 332. Specifically, the enhancement section 333 generates an image that simulates an image in which indigocarmine (that improves the contrast of minute irregular parts on the surface of tissue) is sprayed. More specifically, when the attention pixel represented by the image signal is a recess (hereinafter may be referred to as "groove") formed in the surface of tissue, the enhancement section 333 multiplies the image signal by a gain that increases the degree of blueness. Note that the extracted irregularity information transmitted from the irregularity information acquisition section 320 corresponds to the image signal input from the demosaicing section 332 on a one-to-one basis (on a pixel basis).

Figure 9:
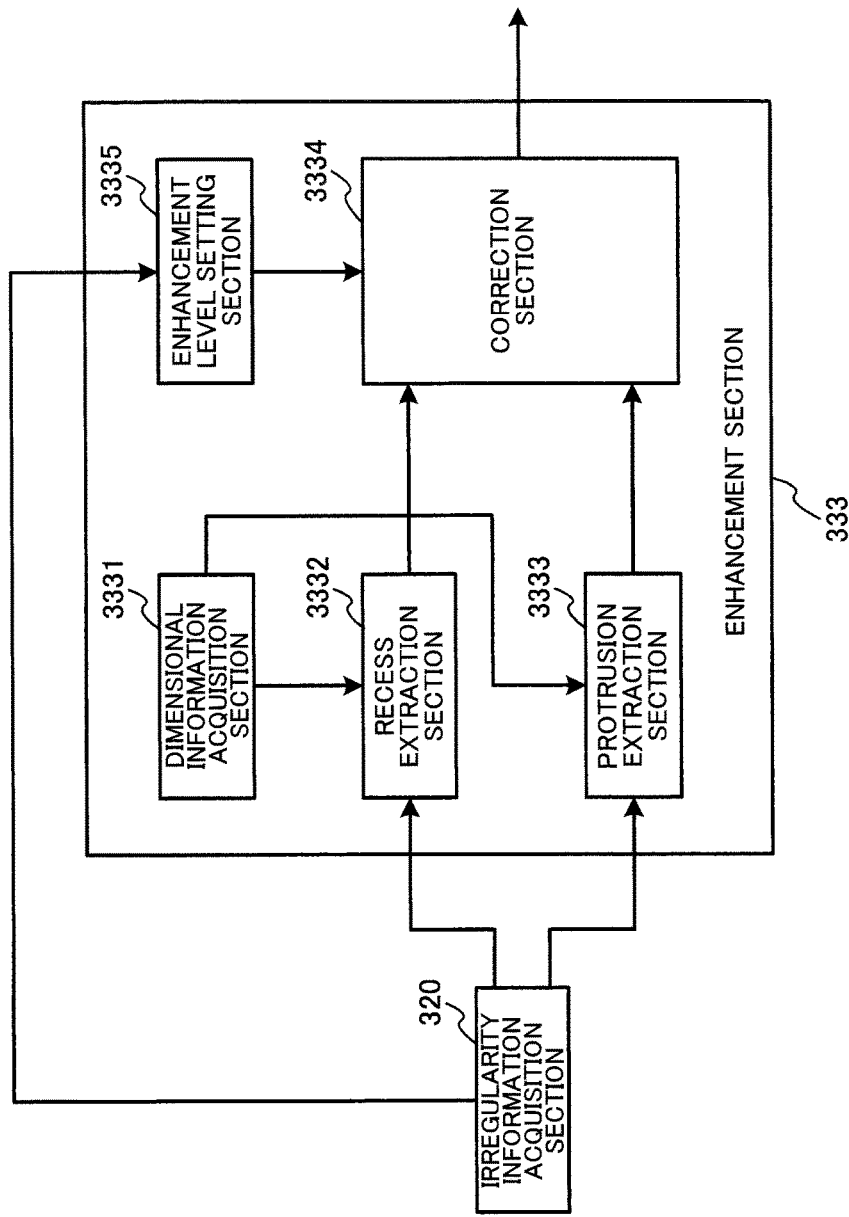
FIG. 9 illustrates a configuration example of an enhancement section.

As illustrated in FIG. 9, the enhancement section 333 includes a dimensional information acquisition section 3331, a recess extraction section 3332, a protrusion extraction section 3333, a correction section 3334, and an enhancement level setting section 3335. Note that the configuration of the enhancement section 333 is not limited to the configuration illustrated in FIG. 9. Various modifications may be made, such as omitting some of the elements illustrated in FIG. 9, or adding other elements.

The dimensional information acquisition section 3331 acquires the known characteristic information (particularly the dimensional information) from the storage section 360 or the like. The recess extraction section 3332 extracts the enhancement target recess from the irregular parts included in (represented by) the extracted irregularity information based on the known characteristic information. The protrusion extraction section 3333 extracts the enhancement target protrusion from the irregular parts included in (represented by) the extracted irregularity information based on the known characteristic information.

The correction section 3334 performs a correction process that improves the visibility of the enhancement target. The details thereof are described later. The correction section 3334 may perform the correction process using the enhancement level that has been set by the enhancement level setting section 3335.

The enhancement process ON/OFF instruction signal is input from the switch 270 or the external I/F section 500 through the control section 340. When the instruction signal instructs not to perform the enhancement process, the enhancement section 333 transmits the image signals input from the demosaicing section 332 to the post-processing section 334 without performing the enhancement process. When the instruction signal instructs to perform the enhancement process, the enhancement section 333 performs the enhancement process.

When the enhancement section 333 performs the enhancement process, the enhancement section 333 detects a groove formed in the surface of tissue from the extracted irregularity information based on the known characteristic information. The known characteristic information represents the width and the depth of a groove formed in the surface of tissue. A minute groove formed in the surface of tissue normally has a width equal to or smaller than several thousand micrometers and a depth equal to or smaller than several hundred micrometers. The width and the depth of the groove formed in the surface of tissue are calculated from the extracted irregularity information.

Figure 10:
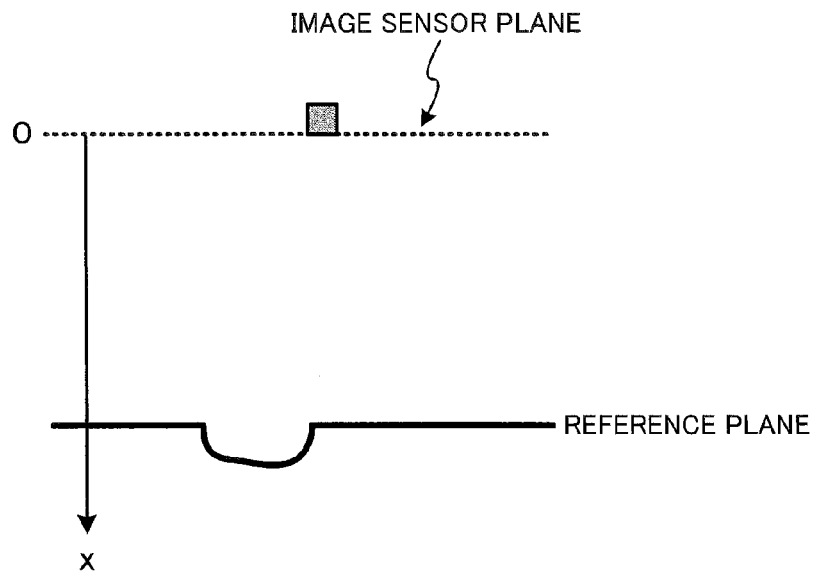
FIG. 10 illustrates an example of extracted irregularity information.

FIG. 10 illustrates one-dimensional extracted irregularity information. The distance from the image sensor to the surface of tissue increases in the depth direction provided that the position (imaging plane) of the image sensor 260 is 0. FIG. 11 illustrates a groove width calculation method. Specifically, the ends of sequential points that are situated deeper than the reference plane and apart from the imaging plane at a distance equal to or larger than a given threshold value x1 (i.e., the points A and B illustrated in FIG. 11) are detected from the extracted irregularity information. In the example illustrated in FIG. 11, the reference plane is situated at the distance x1 from the imaging plane. The number N of pixels corresponding to the points A and B and the points situated between the points A and B is calculated. The average value xave of the distances x1 to xN from the image sensor (at which the points A and B and the points situated between the points A and B are respectively situated) is calculated. The width w of the groove is calculated by the following expression (3). Note that p is the width per pixel of the image sensor 260, and K is the optical magnification that corresponds to the distance xave from the image sensor on a one-to-one basis.

$$w = N \times p \times K \tag{3}$$

Figure 12:
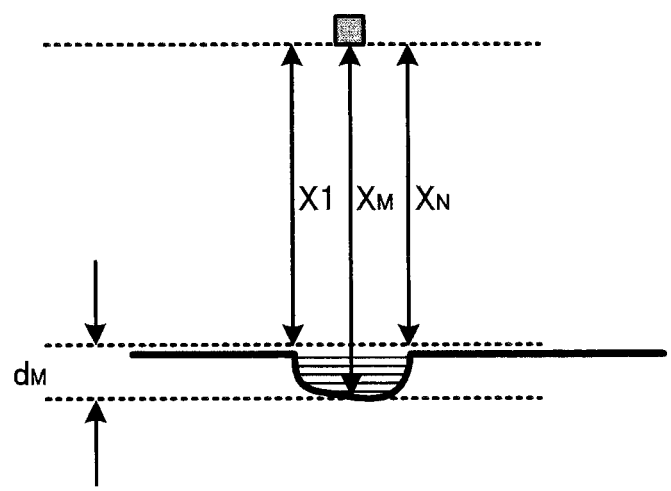
FIG. 12 is a view illustrating a recess depth calculation process.

FIG. 12 illustrates a groove depth calculation method. The depth d of the groove is calculated by the following expression (4). Note that xM is the maximum value among the distances x1 to xN, and xmin is the distance x1 or xN, whichever is smaller.

$$d = xM - x\min 1 \tag{4}$$

The user may arbitrarily set the reference plane (i.e., the plane situated at the distance x1 from the image sensor) through the external I/F section 500. When the width and the depth of the groove thus calculated agree with the known characteristic information, the pixel position of the corresponding image signal is set to be the attention pixel. For example, when the width of the groove is equal to or smaller than 3000 μm, and the depth of the groove is equal to or smaller than 500 μm, the corresponding pixel is set to be the attention pixel. The user may set the threshold values (width and depth) through the external I/F section 500.

The enhancement section 333 thus determines the enhancement target object (i.e., the enhancement target attention pixel in a narrow sense). The enhancement section 333 then multiplies the pixel value of the pixel set to be the attention pixel by a gain coefficient. Specifically, the enhancement section 333 increases the signal value of the B signal of the attention pixel by multiplying the pixel value by the gain coefficient that is equal to or larger than 1, and decreases the signal values of the R signal and the G signal of the attention pixel by multiplying the pixel values by the gain coefficient that is equal to or smaller than 1 This makes it possible to obtain an image in which the degree of blueness of the groove (recess) formed in the surface of tissue is increased (i.e., an image that simulates an image in which indigocarmine is sprayed).

Figure 13A:
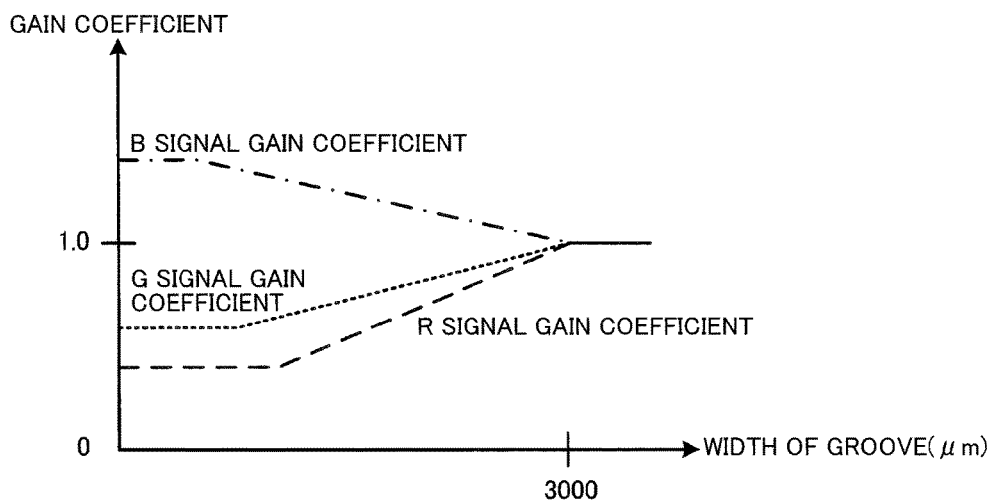
FIGS. 13A and 13B are views illustrating an enhancement level (gain coefficient) setting example when performing an enhancement process on a recess.
Figure 13B:
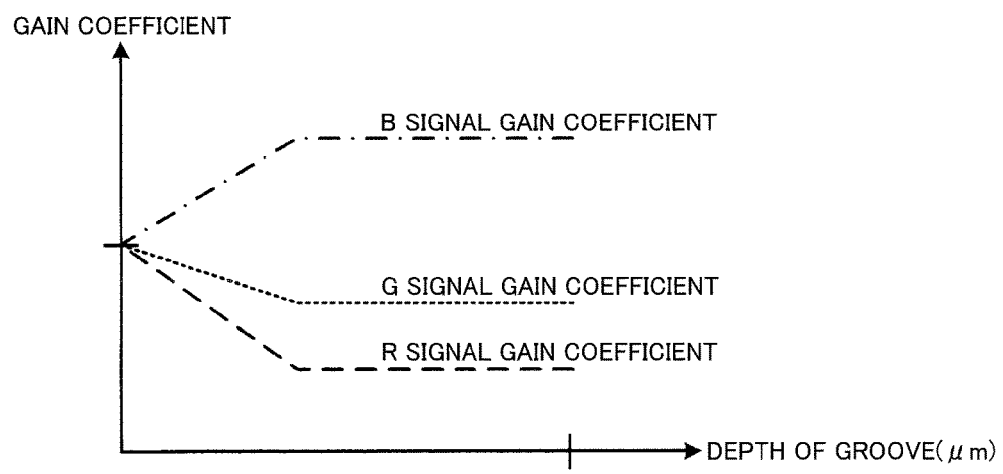

In this case, the enhancement section 333 may uniformly perform the enhancement process on the attention pixels. For example, the enhancement section 333 may perform the enhancement process on the attention pixels using an identical gain coefficient. Note that the enhancement section 333 may perform the enhancement process on the attention pixels in a different way. For example, the enhancement section 333 may perform the enhancement process on the attention pixels while changing the gain coefficient corresponding to the width and the depth of the groove. Specifically, the enhancement section 333 may multiply the pixel value by the gain coefficient so that the degree of blueness decreases as the depth of the groove decreases. This makes it possible to obtain an image that is closer to an image obtained by spraying a dye. FIG. 13B illustrates a gain coefficient setting example when multiplying the pixel value by the gain coefficient so that the degree of blueness decreases as the depth of the groove decreases. Alternatively, when it has been found that a fine structure is useful for finding a lesion, for example, the enhancement level may be increased as the width of the groove decreases (i.e., as the degree of fineness of the structure increases). FIG. 13A illustrates a gain coefficient setting example when increasing the enhancement level as the width of the groove decreases.

Figure 14A:
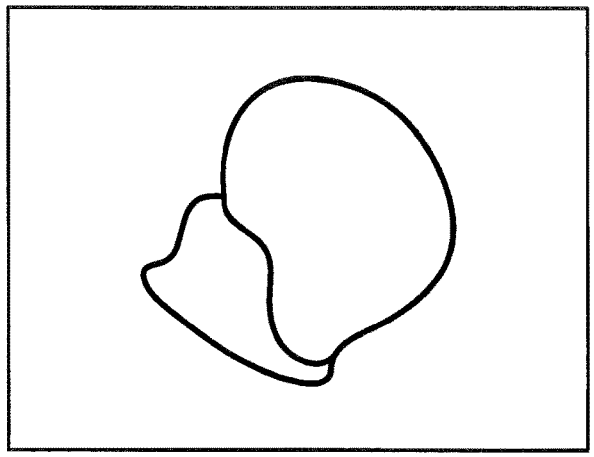
FIGS. 14A and 14B are views illustrating an example of a recess enhancement process.
Figure 14B:
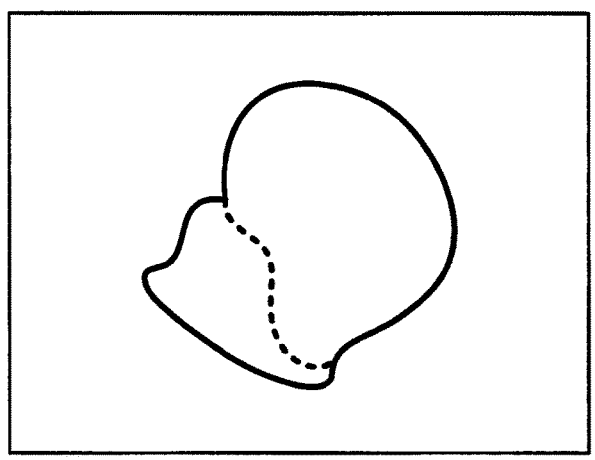

Although an example in which the enhancement process increases the degree of blueness has been described above, the configuration is not limited thereto. For example, the color may be changed corresponding to the depth of the groove (see FIG. 14B). FIG. 14B illustrates an example in which the color is changed along the dotted line. This makes it possible to visually observe the continuity of the groove as compared with the case where the same color is applied to each groove independently of the depth of the groove, and implement a highly accurate diagnosis.

Although an example has been described above in which the enhancement process increases the signal value of the B signal, and decreases the signal values of the R signal and the G signal by multiplying the pixel value by an appropriate gain coefficient, the configuration is not limited thereto. For example, the enhancement process may increase the signal value of the B signal and decrease the signal value of the R signal by multiplying the pixel value by an appropriate gain coefficient, while allowing the signal value of the G signal to remain unchanged. In this case, since the signal values of the B signal and the G signal remain although the degree of blueness of the recess is increased, the structure within the recess is displayed in cyan.

The enhancement section 333 may perform the enhancement process on the entire image instead of performing the enhancement process only on the attention pixels. In this case, the enhancement section 333 performs a process that improves visibility (i.e., a process that increases the gain coefficient) on the area that corresponds to the attention pixel, and performs a process that decreases the gain coefficient, sets the gain coefficient to 1 (original color), or changes the color to a specific color (e.g., a process that improves the visibility of the enhancement target by changing the color to the complementary color of the target color of the enhancement target) on the remaining area, for example. Specifically, the enhancement process according to the first embodiment is not limited to a process that generates an image that simulates an image obtained by spraying indigocarmine, but can be implemented by various processes that improve the visibility of the attention target.

The enhancement section 333 transmits the image signals (that enhance the recesses formed in the surface of tissue) to the post-processing section 334. The post-processing section 334 performs a grayscale transformation process, a color process, and a contour enhancement process on the image signals transmitted from the enhancement section 333 using a grayscale transformation coefficient, a color conversion coefficient, and a contour enhancement coefficient stored in the control section 340. The post-processing section 334 transmits the resulting image signals to the display section 400.

2.4 Distance Information Acquisition Process

Figure 15:
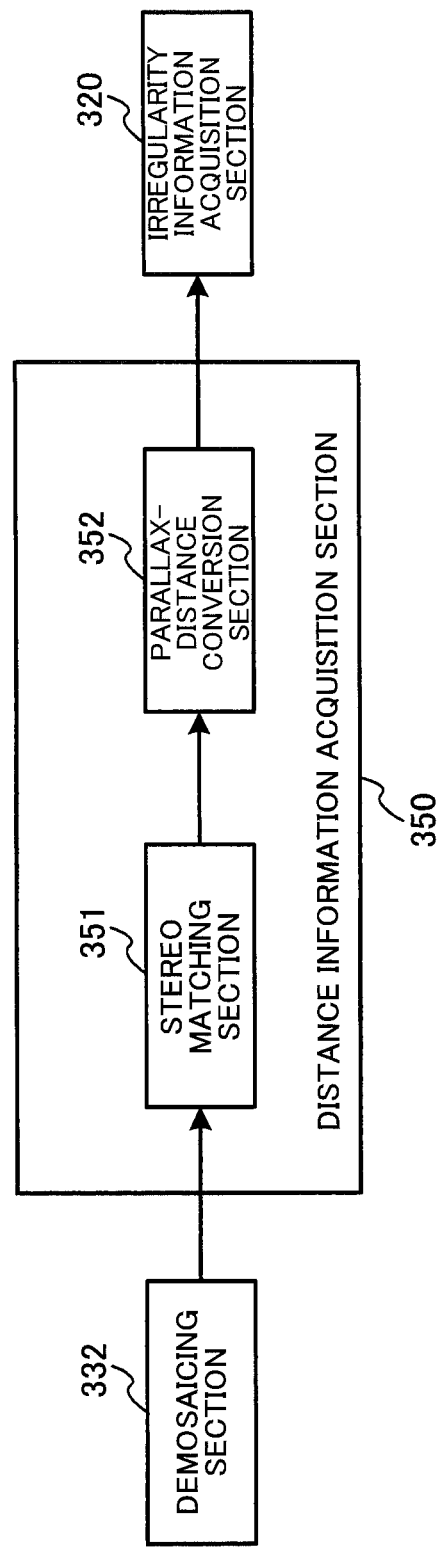
FIG. 15 illustrates a configuration example of a distance information acquisition section.

The distance information acquisition process is described below. As illustrated in FIG. 15, the distance information acquisition section 350 includes a stereo matching section 351 and a parallax-distance conversion section 352. The stereo image preprocessed by the image processing section 330 is input to the stereo matching section 351, and the stereo matching section 351 performs a block matching process on the left image (reference image) and the right image with respect to the processing target pixel and its peripheral area (i.e., a block having a given size) using an epipolar line to calculate parallax information. The parallax-distance conversion section 352 converts the calculated parallax information into the distance information. This conversion process includes a process that corrects the optical magnification of the imaging section 200. The parallax-distance conversion section 352 outputs the distance information to the irregularity information acquisition section 320 as the distance map (having the same pixel size as that of the stereo image in a narrow sense).

The above distance information acquisition process is widely known as a stereo matching process, and detailed description thereof is omitted.

Figure 16:
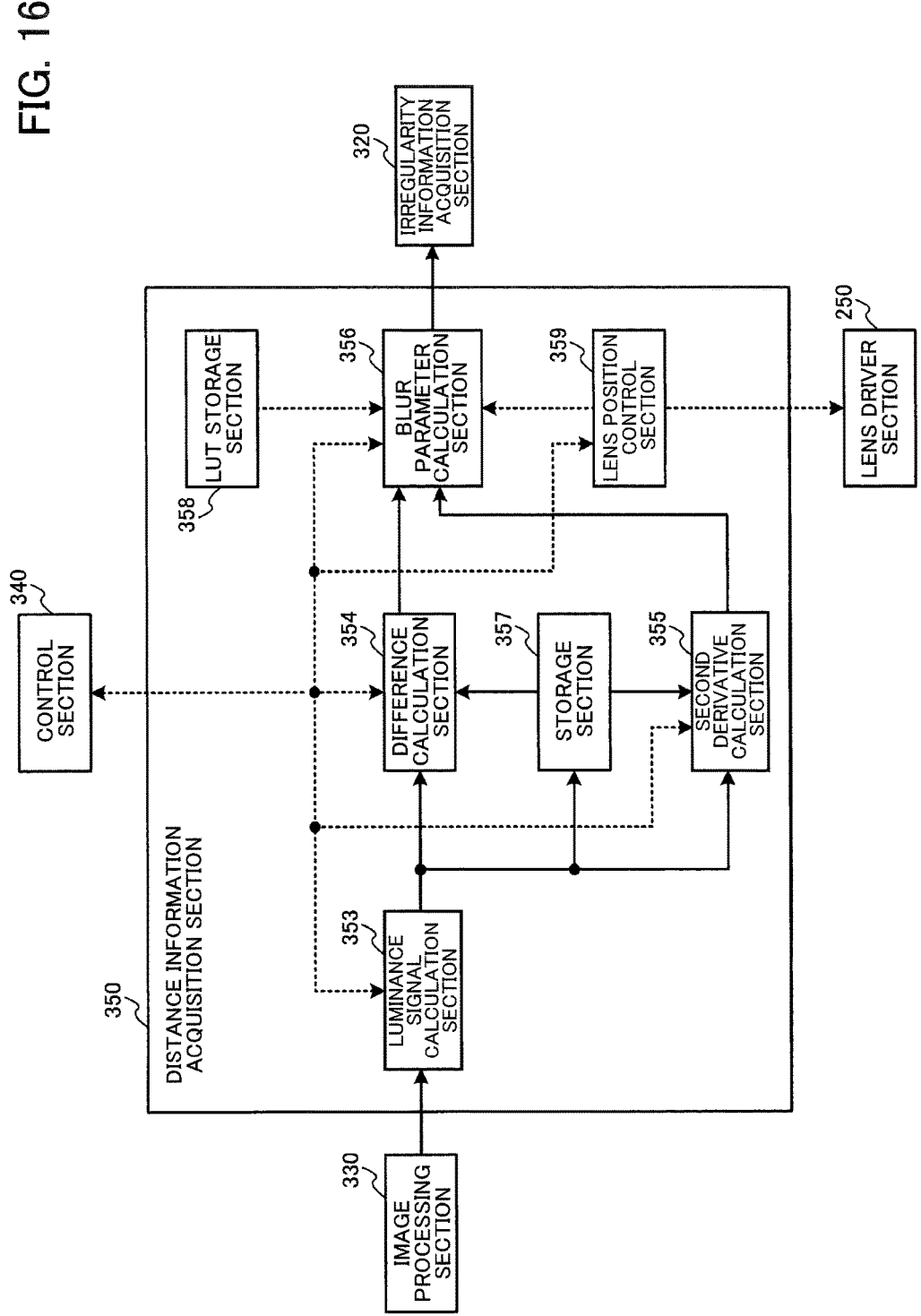
FIG. 16 illustrates another configuration example of a distance information acquisition section.

Note that the distance information acquisition process is not limited to the stereo matching process. A modification is described in detail below with reference to FIG. 16. FIG. 16 illustrates another configuration example of the distance information acquisition section 350. As illustrated in FIG. 16, the distance information acquisition section 350 includes a luminance signal calculation section 353, a difference calculation section 354, a second derivative calculation section 355, a blur parameter calculation section 356, a storage section 357, an LUT storage section 358, and a lens position control section 359. The following description illustrates an example in which one objective lens, one focus lens, and one image sensor are provided, since it is not indispensable to acquire a stereo image.

The luminance signal calculation section 353 calculates a luminance signal Y from the image signals output from the image processing section 330 using the following expression (5) under control of the control section 340.

$$Y=0.299 \times R+0.587 \times G+0.114 \times B \tag{5}$$

The image signals calculated by the luminance signal calculation section 353 are transmitted to the difference calculation section 354, the second derivative calculation section 355, and the storage section 357. The difference calculation section 354 calculates the difference between the luminance signals Y from a plurality of images necessary for calculating a blur parameter. The second derivative calculation section 355 calculates the second derivative of the luminance signals Y (image signals), and calculates the average value of the second derivatives obtained from a plurality of luminance signals Y that differ in blur. The blur parameter calculation section 356 calculates the blur parameter by dividing the difference between the luminance signals Y calculated by the difference calculation section 354 by the average value of the second derivatives calculated by the second derivative calculation section 355.

The storage section 357 stores the luminance signals Y of the first captured image, and the second derivative results thereof. Therefore, the distance information acquisition section 350 can place the focus lens at different positions, and acquire a plurality of luminance signals Y at different times.

The LUT storage section 358 stores the relationship between the blur parameter and the object distance in the form of a look-up table (LUT).

The control section 340 is bidirectionally connected to the luminance signal calculation section 353, the difference calculation section 354, the second derivative calculation section 355, the blur parameter calculation section 356, and the lens position control section 359, and controls the luminance signal calculation section 353, the difference calculation section 354, the second derivative calculation section 355, the blur parameter calculation section 356, and the lens position control section 359.

An object distance calculation method is described below. The lens position control section 359 calculates the optimum focus lens position using a known contrast detection method, a known phase detection method, or the like based on the imaging mode that is set in advance using the external I/F section 500 under control of the control section 340. The lens driver section 250 drives the focus lens 240 to the calculated focus lens position based on the signal output from the lens position control section 359. The image sensor 260 acquires image signals of the object (first image) at the focus lens position to which the focus lens 240 has been driven. The acquired image signals (first image) are stored in the storage section 357 through the image processing section 330 and the luminance signal calculation section 353.

The lens driver section 250 then drives the focus lens 240 to a second focus lens position that differs from the focus lens position at which the image signals have been acquired, and the image sensor 260 acquires image signals of the object (second image) at the focus lens position to which the focus lens 240 has been driven. The acquired image signals (second image) are output to the distance information acquisition section 350 through the image processing section 330.

When the image signals (second image) have been acquired, the blur parameter is calculated. The difference calculation section 354 included in the distance information acquisition section 350 reads the luminance signals Y (image signals) of the first image from the storage section 357, and calculates the difference between the luminance signal Y (image signal) of the first image and the luminance signal Y (image signal) of the second image output from the luminance signal calculation section 353.

The second derivative calculation section 355 calculates the second derivative of the luminance signals Y (image signals) of the second image output from the luminance signal calculation section 353. The second derivative calculation section 355 then reads the luminance signals Y (image signals) of the first image from the storage section 357, and calculates the second derivative of the luminance signals Y. The second derivative calculation section 355 then calculates the average value of the second derivative of the first image and the second derivative of the second image.

The blur parameter calculation section 356 calculates the blur parameter by dividing the difference calculated by the difference calculation section 354 by the average value of the second derivatives calculated by the second derivative calculation section 355.

The blur parameter has a linear relationship with the reciprocal of the object distance. Moreover, the object distance and the focus lens position have a one-to-one relationship. Therefore, the blur parameter and the focus lens position have a one-to-one relationship. The relationship between the blur parameter and the focus lens position is stored in the LUT storage section 358 in the form of a table. The distance information that corresponds to the object distance is represented by the focus lens position.

Therefore, the blur parameter calculation section 356 calculates the object distance to the optical system from the blur parameter by linear interpolation using the blur parameter and the information about the table stored in the LUT storage section 358. The blur parameter calculation section 356 thus calculates the object distance that corresponds to the blur parameter. The calculated object distance is output to the irregularity information acquisition section 320 as the distance information.

Note that the distance information acquisition process may be implemented in various other ways. For example, the distance information may be acquired (calculated) by a Time-of-Flight method that utilizes infrared light or the like. When using the Time-of-Flight method, blue light may be used instead of infrared light, for example.

2.5 Configuration Example Using Software

Although the first embodiment has been described taking an example in which each section of the image processing section 300 is implemented by hardware, the configuration is not limited thereto. For example, a CPU may perform the process of each section on the image signals acquired in advance using an imaging device and the distance information. Specifically, the process of each section may be implemented by means of software by causing the CPU to execute a program. Alternatively, part of the process performed by each section may be implemented by means of software.

When separately providing the imaging section and the AD conversion section, and implementing the process of each section of the image processing section 300 excluding the AD conversion section by means of software, a known computer system (e.g., work station or personal computer) may be used as the image processing device. A program (image processing program) that implements the process of each section of the image processing section 300 may be provided in advance, and executed by the CPU of the computer system.

Figure 17:
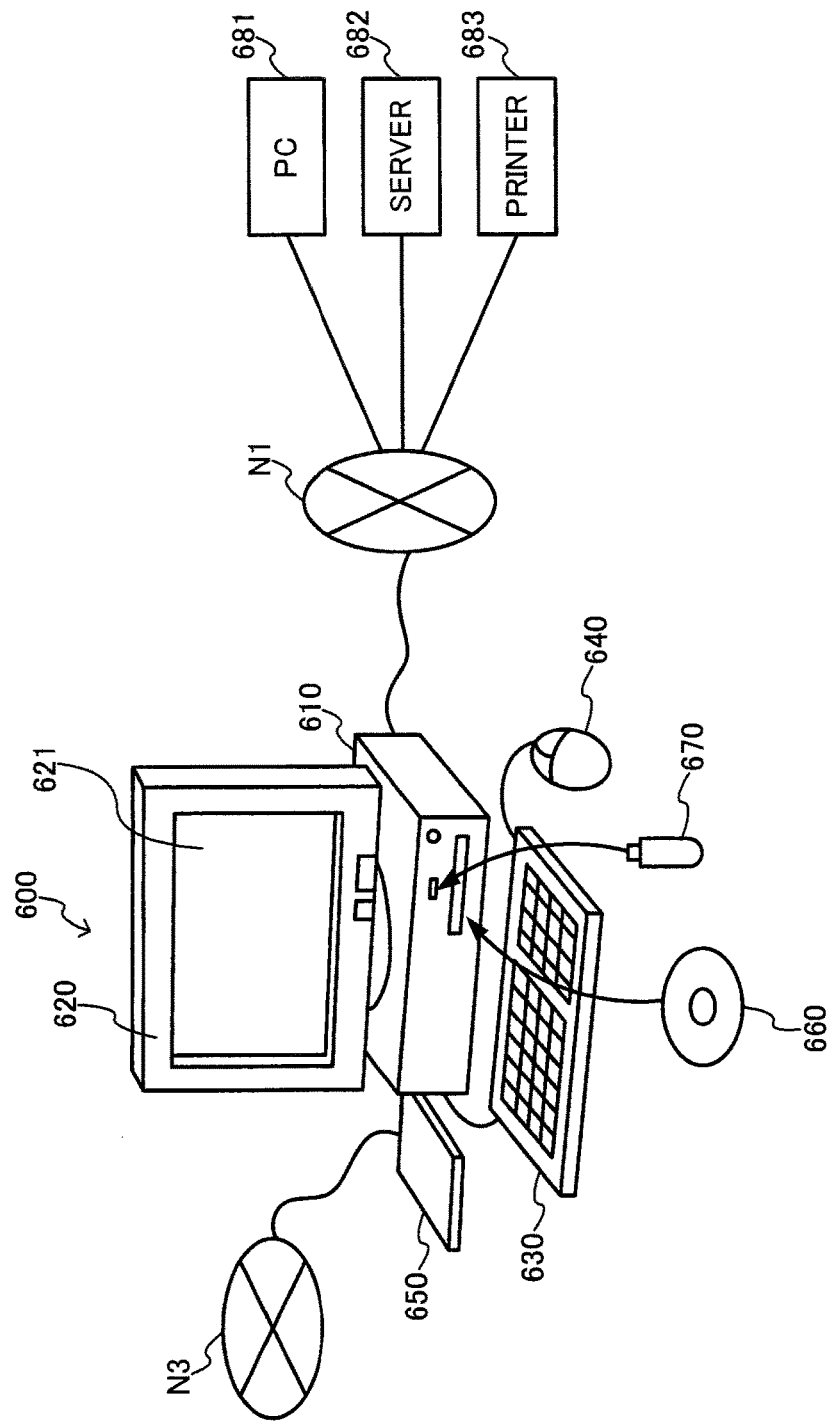
FIG. 17 illustrates a configuration example of a computer system.
Figure 18:
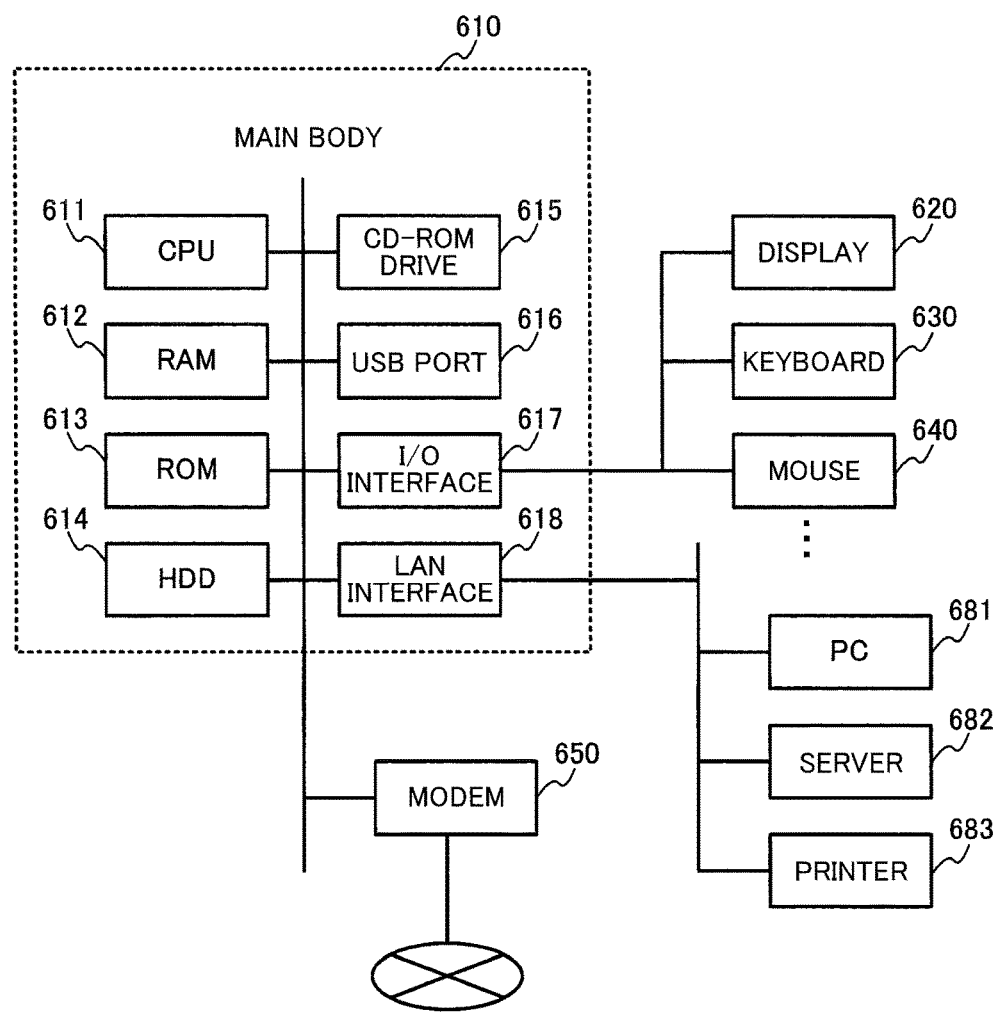
FIG. 18 illustrates a configuration example of a computer system.

FIG. 17 is a system configuration diagram illustrating the configuration of a computer system 600 according to a modification, and FIG. 18 is a block diagram illustrating the configuration of a main body 610 of the computer system 600. As illustrated in FIG. 17, the computer system 600 includes the main body 610, a display 620 that displays information (e.g., image) on a display screen 621 based on instructions from the main body 610, a keyboard 630 that allows the user to input information to the computer system 600, and a mouse 640 that allows the user to designate an arbitrary position on the display screen 621 of the display 620.

As illustrated in FIG. 18, the main body 610 of the computer system 600 includes a CPU 611, a RAM 612, a ROM 613, a hard disk drive (HDD) 614, a CD-ROM drive 615 that receives a CD-ROM 660, a USB port 616 to which a USB memory 670 is removably connected, an I/O interface 617 that connects the display 620, the keyboard 630, and the mouse 640, and a LAN interface 618 that is used to connect to a local area network or a wide area network (LAN/WAN) N1.

The computer system 600 is connected to a modem 650 that is used to connect to a public line N3 (e.g., Internet). The computer system 600 is also connected to a personal computer (PC) 681 (i.e., another computer system), a server 682, a printer 683, and the like via the LAN interface 618 and the local area network or the large area network N1.

The computer system 600 implements the image processing device by reading an image processing program (e.g., an image processing program that implements a process described below with reference to FIGS. 19 to 21) recorded on a given recording device, and executing the image processing program. The given recording device may be an arbitrary recording device that records the control program that can be read by the computer system 600, such as the CD-ROM 660, the USB memory 670, a portable physical device (e.g., MO disk, DVD disk, flexible disk (FD), magnetooptical disk, or IC card), a stationary physical device (e.g., HDD 614, RAM 612, or ROM 613) that is provided inside or outside the computer system 600, or a communication device that temporarily stores a program during transmission (e.g., the public line N3 connected via the modem 650, or the local area network or the wide area network N1 to which the computer system (PC) 681 or the server 682 is connected). Specifically, the image processing program is recorded on a recording device (e.g., portable physical device, stationary physical device, or communication device) in a computer-readable way. The computer system 600 implements the image processing device by reading the image processing program from such a recording device, and executing the image processing program. Note that the image processing program need not necessarily be executed by the computer system 600. The invention may be similarly applied to the case where the computer system (PC) 681 or the server 682 executes the image processing program, or the computer system (PC) 681 and the server 682 execute the image processing program in cooperation.

Figure 19:
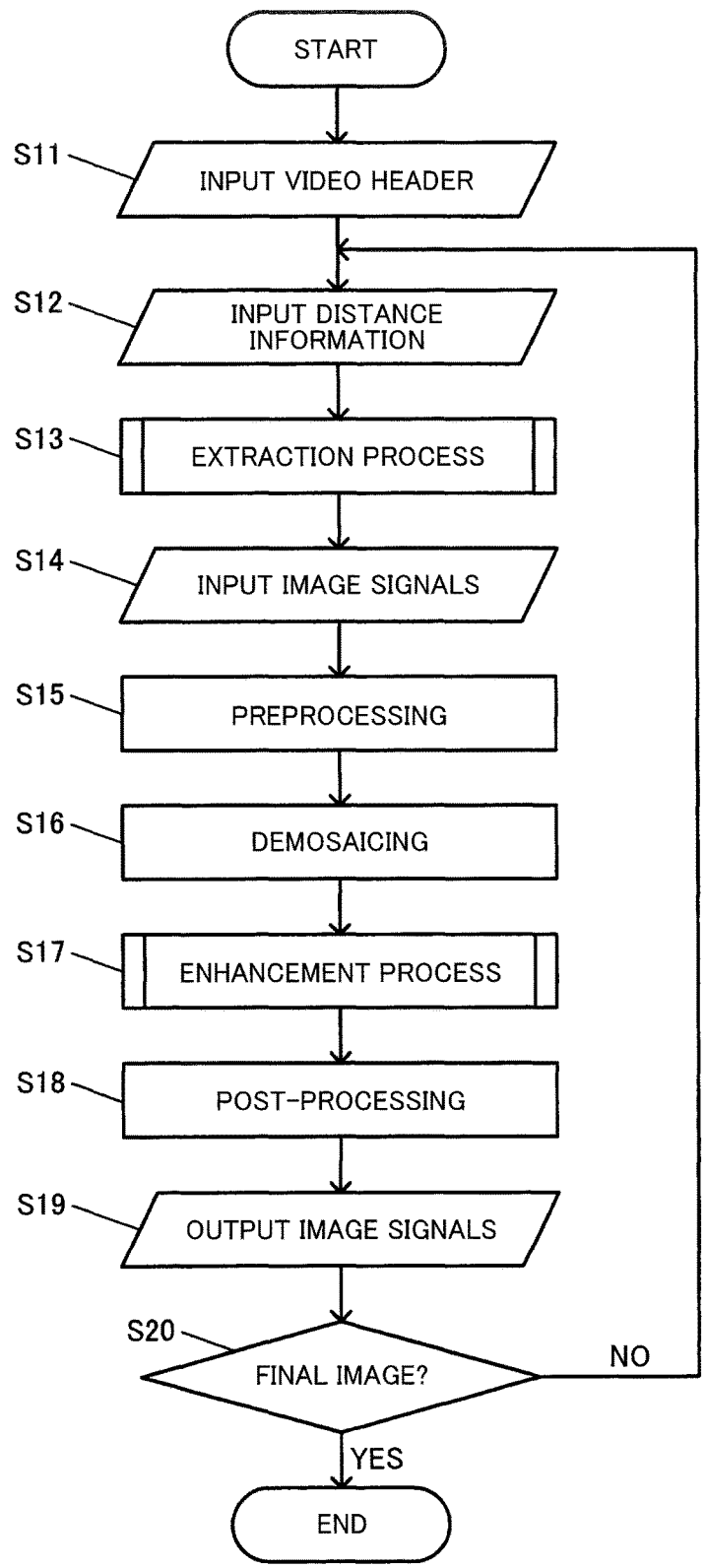
FIG. 19 is a flowchart illustrating a process according to one embodiment of the invention.

FIG. 19 is a flowchart illustrating the entire process according to the first embodiment. In the step S11, header information (e.g., the optical magnification (with respect to the distance information) of the imaging device, and the imaging conditions) is input. The distance information that represents the distance from the imaging plane of the imaging device to the object is input (S12). The extracted irregularity information about the surface of tissue is extracted from the distance information (described in detail below with reference to FIG. 20) (S13). The image signals are input (S14). The preprocess is performed (S15), and the demosaicing process is performed (S16). A process that improves the contrast of the minute irregular parts on the surface of tissue is performed (described in detail below with reference to FIG. 21) (S17). The post-process is performed (S18), and the image that has been subjected to the enhancement process is output (S19). Whether or not the process has been performed on the final image is determined (S20). When it has been determined that the process has not been performed on the final image, the above process is performed on the next image signals from the step S12. When it has been determined that the process has been performed on the final image, the process is terminated.

Figure 20:
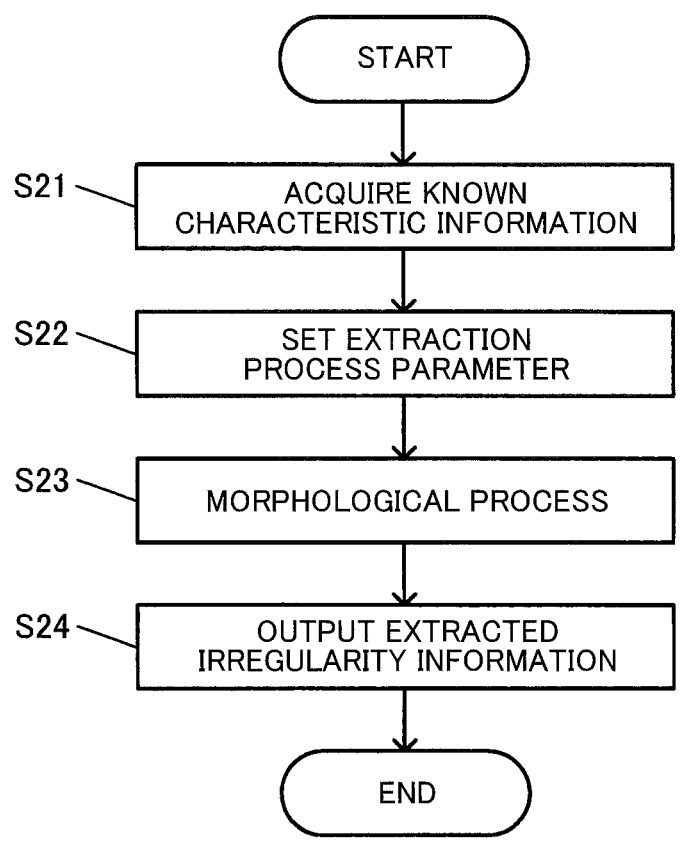
FIG. 20 is a flowchart illustrating an extracted irregularity information extraction process.

FIG. 20 is a flowchart illustrating the extraction process. The known characteristic information is acquired from the storage section 360 or the like (S21). The known characteristic information in a narrow sense refers to information for specifying the dimensional characteristics of the extraction target irregular part. The extraction process parameter used for the extraction process is set based on the acquired known characteristic information (S22). Examples of the extraction process parameter include the size of the structural element used for the morphological process, and the characteristics of the filter used for the filtering process (see above). The extraction process (e.g., morphological process) that utilizes the extraction process parameter is performed (S23), and the extracted irregularity information is output (S24).

Figure 21:
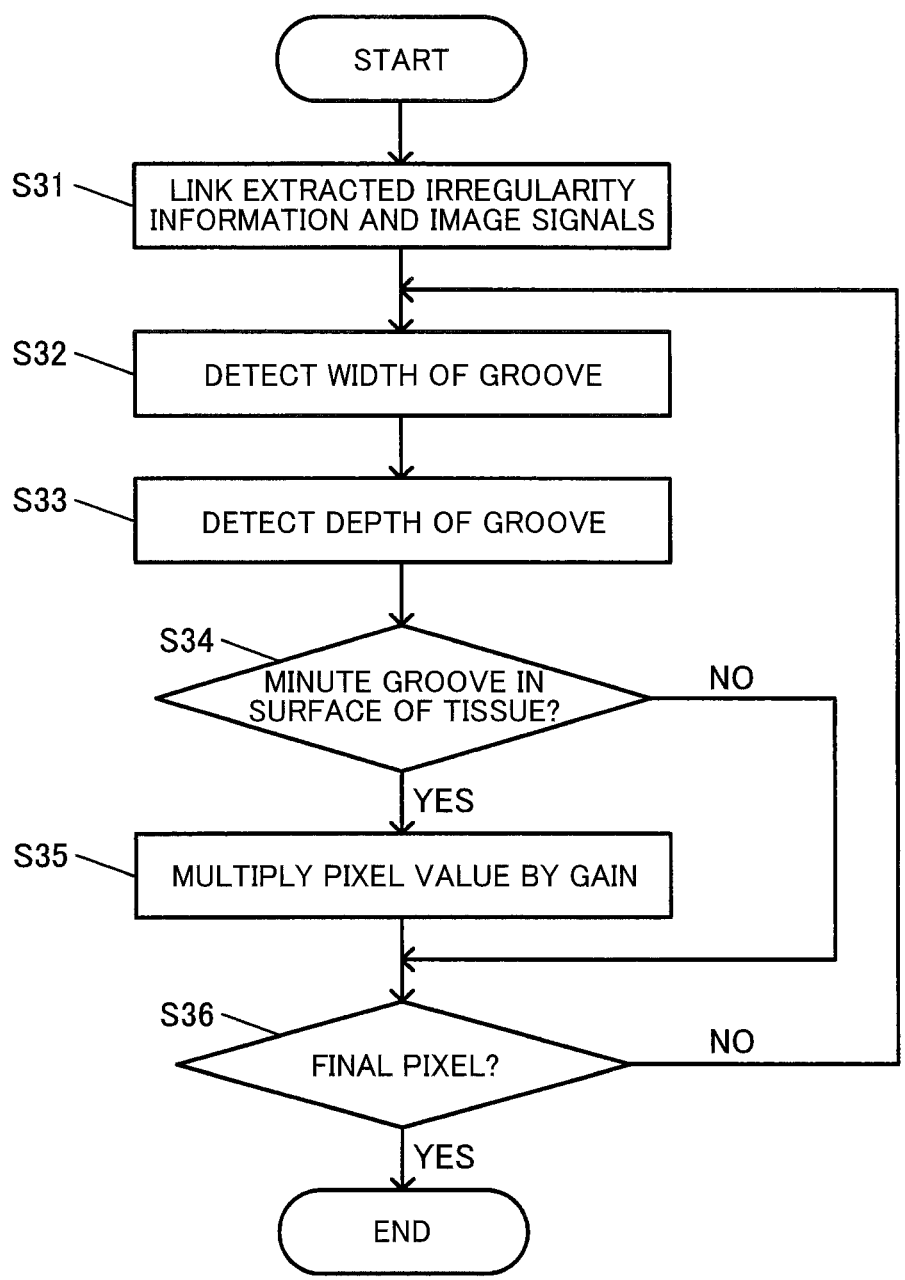
FIG. 21 is a flowchart illustrating an enhancement process.

FIG. 21 is a flowchart illustrating the enhancement process. The extracted irregularity information and the pixels (image signals) are linked on a one-to-one basis (S31). The width w of the groove is detected (calculated) using the expression (3) (S32). The depth d of the groove is detected (calculated) using the expression (4) (S33). Whether or not the groove detected based on the known characteristic information is the enhancement target (minute groove) is determined (S34). When it has been determined that the groove detected based on the known characteristic information is the enhancement target, the step S35 is performed. When it has been determined that the groove detected based on the known characteristic information is not the enhancement target, the step S36 is performed. When it has been determined that the groove detected based on the known characteristic information is the enhancement target (Yes in S34), the pixel value is multiplied by the gain so as to increase the degree of blueness of the enhancement target pixel (S35). When it has been determined that the groove detected based on the known characteristic information is not the enhancement target (No in S34), or after the step S35 has been performed, whether or not the process has been performed on the final pixel is deteimined (S36). When it has been determined that the process has not been performed on the final pixel, the above process is repeated from the step S32.

According to the first embodiment, the contrast of minute irregular parts (irregularities) present on the surface of tissue is increased (i e, minute irregular parts are enhanced) based on the extracted irregularity information about the surface of tissue, and the known characteristic information about a lesion. This makes it possible to accurately increase the contrast of minute irregular parts (i.e., enhance minute irregular parts), and obtain an image with high visibility, without performing a complex dye-spraying operation.

Although an example in which the degree of blueness of a groove is enhanced has been described above, it is also possible to allow the user to designate the enhancement process according to his/her preference. For example, the enhancement process based on the difference in luminance, the enhancement process that enhances the G signal component, the enhancement process that changes the color to the complementary color of the background color, or the like may be performed. Although an example that utilizes a frame sequential imaging method has been described above, a primary-color Bayer imaging method, a complementary-color single-chip imaging method, a primary-color double-chip imaging method, a primary-color triple-chip imaging method, or the like may also be used. Although an example in which the light source emits normal light has been described above, the light source may emit special light (e.g., narrow band imaging (NBI)), for example.

According to the first embodiment, the image processing device includes the image acquisition section 310 that acquires a captured image that includes an image of an object, the captured image being an image captured by the imaging section 200, the distance information acquisition section 350 that acquires the distance information based on the distance from the imaging section 200 to the object when the imaging section 200 captured the captured image, the irregularity information acquisition section 320 that acquires the extracted irregularity information from the acquired distance information, the extracted irregularity information being information that represents irregular parts extracted from the object, and the enhancement section 333 that performs the enhancement process on the enhancement target, the enhancement target being an irregular part among the irregular parts represented by the extracted irregularity information that agrees with the characteristics specified by the known characteristic information, the known characteristic information being information that represents known characteristics relating to the structure of the object (see FIGS. 2 and 8).

The term "distance information" used herein refers to information that is acquired based on the distance from the imaging section 200 to the object. For example, when implementing triangulation using a stereo optical system (see above), the distance with respect to an arbitrary point in a plane that connects two lenses (i.e., the objective lenses 230-1 and 230-2 illustrated in FIG. 2) that produce a parallax may be used as the distance information. When using the Time-of-Flight method described later in connection with the second embodiment and the like, the distance with respect to each pixel position in the plane of the image sensor is acquired as the distance information, for example. In such a case, the distance measurement reference point is set to the imaging section 200. Note that the distance measurement reference point may be set to an arbitrary position other than the imaging section 200, such as an arbitrary position within the three-dimensional space that includes the imaging section and the object. The distance information acquired using such a reference point is also intended to be included within the term "distance information".

The distance from the imaging section 200 to the object may be the distance from the imaging section 200 to the object in the depth direction, for example. For example, the distance from the imaging section 200 to the object may be the distance from the imaging section 200 to the object in the direction of the optical axis of the imaging section 200. When the viewpoint is set in the direction perpendicular to the optical axis (see FIG. 6A), the distance from the imaging section 200 to the object may be the distance from the imaging section 200 to the object observed from the viewpoint (e.g., the distance from the imaging section 200 to the object in the vertical direction (see the arrow) in the example illustrated in FIG. 6A).

For example, the distance information acquisition section 350 may transform the coordinates of each corresponding point in a first coordinate system in which a first reference point of the imaging section 200 is the origin, into the coordinates of each corresponding point in a second coordinate system in which a second reference point within the three-dimensional space is the origin, using a known coordinate transformation process, and measure the distance based on the coordinates obtained by transformation. In this case, the distance from the second reference point to each corresponding point in the second coordinate system is identical with the distance from the first reference point to each corresponding point in the first coordinate system (i.e., the distance from the imaging section to each corresponding point).

The distance information acquisition section 350 may set a virtual reference point at a position that can maintain a relationship similar to the relationship between the distance values of the pixels on the distance map acquired when setting the reference point to the imaging section 200, to acquire the distance information based on the distance from the imaging section 200 to each corresponding point. For example, when the actual distances from the imaging section 200 to three corresponding points are respectively "3", "4", and "5", the distance information acquisition section 350 may acquire distance information "1.5", "2", and "2.5" respectively obtained by halving the actual distances "3", "4", and "5" while maintaining the relationship between the distance values of the pixels. In this case, the irregularity information acquisition section 320 uses a different extraction process parameter as compared with the case of setting the reference point to the imaging section 200. Specifically, since it is necessary to use the distance information when determining the extraction process parameter, the extraction process parameter is determined in a different way when the distance measurement reference point has changed (i.e., when the distance information is represented in a different way). For example, when extracting the extracted irregularity information using the morphological process (see above), the size of the structural element (e.g., the diameter of a sphere) used for the extraction process is adjusted, and the irregular part extraction process is performed using the structural element that has been adjusted in size.

The term "enhancement target" used herein refers to an object within the captured image that corresponds to an irregular part among the irregular parts represented by the extracted irregularity information that agrees with the characteristics specified by the known characteristic information. Specifically, the enhancement process according to first embodiment is performed on the captured image in a narrow sense, and is not performed on the extracted irregularity information.

The above configuration makes it possible to perform the enhancement process that utilizes the known characteristic information. As described above, a minute irregular part or the like included in an in vivo image that is useful for finding an early lesion cannot be effectively enhanced using a known enhancement process (e.g., a process that enhances a high-frequency component). It is also difficult to enhance a minute irregular part when performing the enhancement process on an image other than an in vivo image. Since the method according to first embodiment can appropriately set the enhancement target pixel (attention pixel) within the captured image, and the enhancement level, it is possible to enhance the desired irregular part. Since it is unnecessary to effect a change in the object (e.g., by spraying a dye) by generating an image that simulates an in vivo image obtained by spraying a dye, it is unnecessary to take account of a decrease in visibility of an object other than the enhancement target, and invasiveness when performing the process on tissue, for example. Note that the extracted irregularity information in a narrow sense may represent an irregular image in which the number of pixels corresponds to the distance map or the captured image (e.g., the same number of pixels as that of the distance map or the captured image), and each pixel value is a value that corresponds to a protrusion or a recess. For example, a value that corresponds to a protrusion may be a positive value, a value that corresponds to a recess may be a negative value, and the absolute value of each value may increase as the height of the protrusion increases, or the depth of the recess increases. Note that the extracted irregularity information is not limited to the irregular image, but may be another type of information.

The enhancement section 333 may include the dimensional information acquisition section 3331 that acquires the dimensional information as the known characteristic information, the dimensional information representing at least one of the width and the depth of a recess of an object that is determined to be the enhancement target, the recess extraction section 3332 that extracts extracted recess information about a recess among the irregular parts included in the extracted irregularity information that agrees with the characteristics specified by the dimensional information, and the correction section 3334 that performs a process that corrects at least one of a color, luminance, and contrast on the recess that is represented by the extracted recess information (see FIG. 9).

The distance information may be the distance map, for example. The term "distance map" used herein refers to a map in which the distance (depth) to the object in the Z-axis direction (i.e., the direction of the optical axis of the imaging section 200) is specified for each point (e.g., each pixel) in the XY plane, for example. In this case, the width of the recess corresponds to the distance between the two end-points of the recess in the XY plane. The depth of the recess (and the height of the protrusion described later) corresponds to the distance between the reference plane of the recess and the point of the recess that is situated furthest from (or the point of the protrusion that is situated closest to) the imaging section 200 in the Z-axis direction. Note that the width w is calculated while making corrections using the pixel pitch, the imaging magnification, and the like (as described above with reference to the expression (3)), for example.

This makes it possible to perform the enhancement process on a recess (groove) that has a specific width or a specific depth, or both. It is considered that a groove structure having a specific width and a specific depth is useful for finding an early lesion when observing tissue, and is useful for determining the degree of wear of an industrial part when observing an industrial part, for example. Therefore, it is highly useful to perform the enhancement process on such a groove structure. Note that the contrast correction process is described later in connection with the third embodiment.

The enhancement section 333 may include the dimensional information acquisition section 3331 that acquires the dimensional information as the known characteristic information, the dimensional information representing at least one of the width and the depth of a recess of an object that is determined to be the enhancement target, the enhancement level setting section 3335 that sets the enhancement level of the enhancement process based on the dimensional information, and the correction section 3334 that performs a process that corrects at least one of a color, luminance, and contrast on the captured image based on the extracted irregularity information and the enhancement level (see FIG. 9).

The enhancement level of the enhancement process in a narrow sense may be the gain coefficient (see above). Note that the enhancement level is not limited thereto. For example, when performing a color conversion process that converts the color of the visibility-improving target into a specific color, and converts the color of the remaining area into the complementary color of the specific color, the enhancement level setting process also includes the specific color setting process and the like.

This makes it possible to perform the enhancement process on the captured image (e.g., the entire captured image) without limiting the enhancement target to a specific recess. Since the enhancement process according to the first embodiment is intended to increase the visibility of a specific recess, it may be useful to decrease the visibility of another area (or the remaining area). Such a method can be implemented by changing the enhancement level corresponding to the degree of agreement with the characteristics specified by the dimensional information, for example.

The enhancement level setting section 3335 may increase the enhancement level set to a recess included in the extracted irregularity information as the degree of agreement of the width and the depth of the recess with the dimensional information increases.

This makes it possible to increase the enhancement level as the degree of agreement with the enhancement target characteristics increases, and efficiently improve visibility. This process may be implemented by setting the gain coefficient (see FIG. 13A) as the enhancement level.

The enhancement level setting section 3335 may decrease the enhancement level set to a recess included in the extracted irregularity information as the depth of the recess decreases.

This makes it possible to change the enhancement level corresponding to the depth of the recess. This method is particularly useful when generating an image that simulates an image obtained by spraying indigocarmine. It is known that indigocarmine accumulates in a groove having specific dimensions. Specifically, the degree of blueness decreases as the depth of the groove decreases. Therefore, it is possible to generate an image that simulates an image obtained by spraying a chemical with higher reproducibility by decreasing the enhancement level (e.g., the gain coefficient for the B signal component) as the depth of the groove decreases (see FIG. 13B).

The image processing device may include an input section (e.g., the external I/F section 500 illustrated in FIG. 2) for inputting the known characteristic information that is information that represents the known characteristics relating to the structure of the object.

This makes it possible to use information input by the user in addition to the information that is stored in advance as the known characteristic information, and effectively enhance the enhancement target intended by the user, for example.

The imaging section 200 may include a plurality of viewpoints, the image acquisition section 310 may acquire a plurality of captured images that respectively correspond to the plurality of viewpoints, and the distance information acquisition section 350 may acquire the distance information based on parallax information obtained from the plurality of captured images acquired by the image acquisition section 310.

This makes it possible for the image processing device to acquire the distance information based on the parallax image. Note that the distance information need not necessarily be acquired using the stereo matching process. Various modifications may be made.

Note that part or most of the process performed by the image processing device and the like according to the first embodiment may be implemented by a program. In this case, the image processing device and the like according to the first embodiment are implemented by causing a processor (e.g., CPU) to execute a program. Specifically, a program stored in a non-transitory information storage device is read, and executed by a processor (e.g., CPU). The information storage device (computer-readable device) stores a program, data, and the like. The function of the information storage device may be implemented by an optical disk (e.g., DVD or CD), a hard disk drive (HDD), a memory (e.g., memory card or ROM), or the like. The processor (e.g., CPU) performs various processes according to the first embodiment based on the program (data) stored in the information storage device. Specifically, a program that causes a computer (i.e., a device that includes an operation section, a processing section, a storage section, and an output section) to function as each section according to the first embodiment (i.e., a program that causes a computer to execute the process implemented by each section) is stored in the information storage device.

The image processing device and the like according to the embodiments of the invention may include a processor and a memory. The processor may be a central processing unit (CPU), for example. Note that the processor is not limited to a CPU. Various types of processors such as a graphics processing unit (GPU) and a digital signal processor (DSP) may also be used. The processor may be a hardware circuit such as an application specific integrated circuit (ASIC). The memory stores a computer-readable instruction. Each section of the image processing device and the like according to the embodiments of the invention is implemented by causing the processor to execute the instruction. The memory may be a semiconductor memory (e.g., SRAM or DRAM), a register, a hard disk, or the like. The instruction may be an instruction included in an instruction set of a program, or may be an instruction that causes a hardware circuit of the processor to operate.

3. Second Embodiment

The second embodiment is described below. The processes performed by the elements other than the enhancement section 333 are the same as those described above in connection with the first embodiment, and detailed description thereof is omitted.

The enhancement section 333 performs the enhancement process that increases the degree of redness of the detected protrusion (i.e., an early lesion in the form of a protrusion). A part that protrudes as compared with the reference plane is detected to be a protrusion in the same manner as in the first embodiment. Whether or not the detected protrusion is the enhancement target is determined based on the known characteristic information. The known characteristic information may be information that represents that the size of a protrusion is equal to or less than 10 mm. Specifically, since a lesion having a size equal to or less than 10 mm is missed with high probability, a protrusion having a size equal to or less than 10 mm is determined to be the enhancement target.

Figure 22:
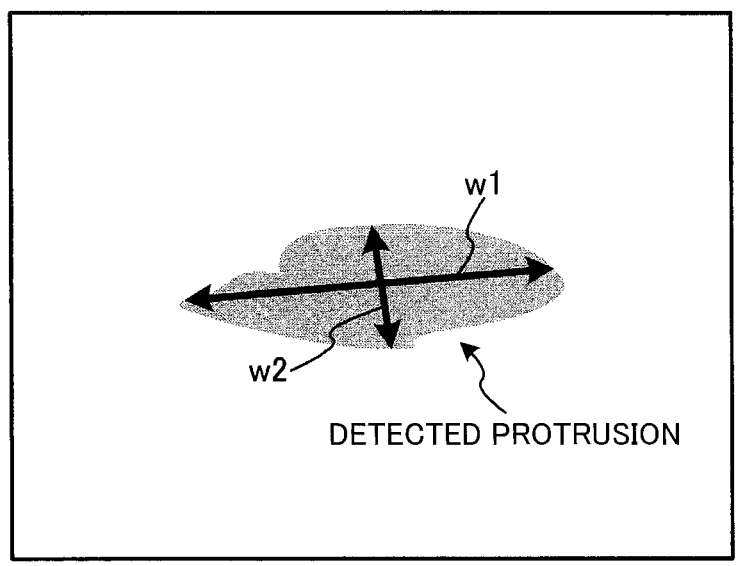
FIG. 22 is a view illustrating a protrusion width calculation process.
Figure 23A:
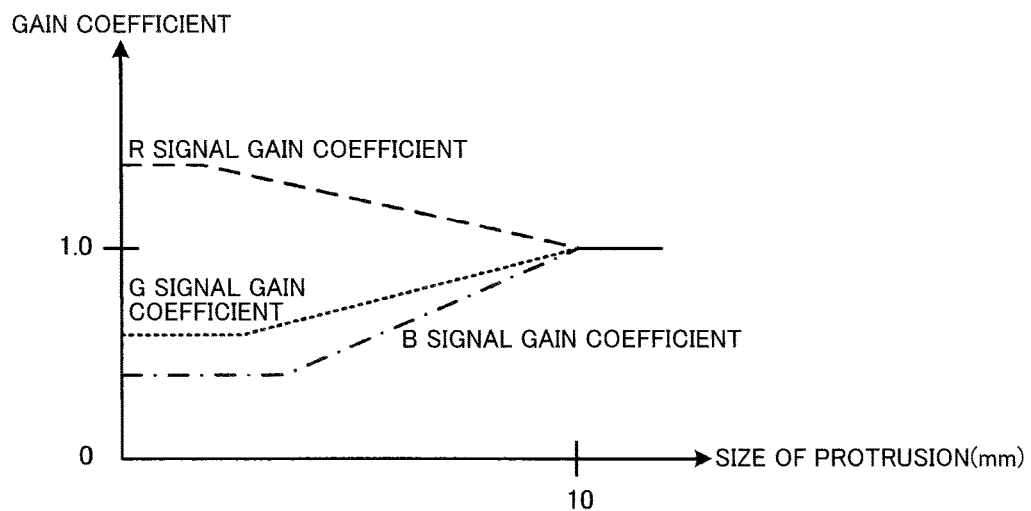
FIGS. 23A and 23B are views illustrating an enhancement level (gain coefficient) setting example when performing an enhancement process on a protrusion.

The size of the protrusion is calculated as described below. Specifically, the width of the protrusion in one-dimensional direction is calculated in the same manner as in the case of detecting the width w of a groove (see the first embodiment). As illustrated in FIG. 22, the width w1 in the long side direction (when observed in two dimensions) is determined to be the size of the protrusion. The enhancement section 333 performs the enhancement process on the protrusion that has been determined to be the enhancement target so that that the degree of redness increases (by multiplying the gain so that the R signal increases, and the G signal and the B signal decrease). The gain coefficient may be set so that the enhancement level increases as the size of the protrusion decreases. FIG. 23A illustrates the relationship between the size of the protrusion and each signal. In this case, since a small lesion that is likely to be missed is enhanced to a large extent, it is possible to prevent a situation in which the lesion is missed.

Figure 23B:
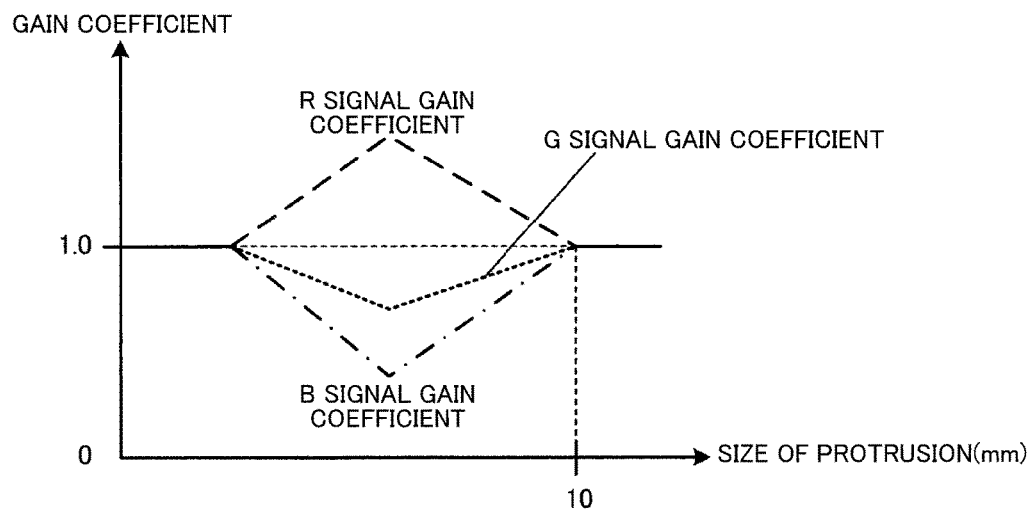

Note that the enhancement process is not limited thereto. For example, the gain coefficients illustrated in FIG. 23B may be used. Specifically, the enhancement level (gain coefficient) is decreased when the size of the protrusion is too small. It is likely that a small protrusion is missed. However, a protrusion that is too small may be noise. Even when a protrusion that is too small is an early lesion, it is likely that it is unnecessary to enhance the protrusion since the degree of severity is low. Therefore, such a small lesion is not enhanced by utilizing the gain coefficients illustrated in FIG. 23B. Note that the user may set the size of a protrusion that is determined to be the enhancement target, the enhancement level, and the like.

The enhancement process according to the second embodiment need not necessarily increase the degree of redness of the protrusion. For example, the enhancement process based on the difference in luminance, the enhancement process that enhances the G signal component, the enhancement process that changes the color to the complementary color of the background color, or the like may also be used in the same manner as in the first embodiment.

According to the second embodiment, the enhancement section 333 included in the image processing device includes the dimensional information acquisition section 3331 that acquires the dimensional information as the known characteristic information, the dimensional information representing at least one of the width and the height of a protrusion of an object that is determined to be the enhancement target, the protrusion extraction section 3333 that extracts extracted protrusion information about a protrusion among the irregular parts included in the extracted irregularity information that agrees with the characteristics specified by the dimensional information, and the correction section 3334 that performs a process that corrects at least one of a color, luminance, and contrast on the protrusion that is represented by the extracted protrusion information (see FIG. 9).

This makes it possible to perform the enhancement process on a protrusion that has a specific width or a specific height, or both. Specific examples of the protrusion vary corresponding to the object. When capturing an in vivo image, the protrusion may be a polyp or the like.

The enhancement section 333 may include the dimensional information acquisition section 3331 that acquires the dimensional information as the known characteristic information, the dimensional information representing at least one of the width and the height of a protrusion of an object that is determined to be the enhancement target, the enhancement level setting section 3335 that sets the enhancement level of the enhancement process based on the dimensional information, and the correction section 3334 that performs a process that corrects at least one of a color, luminance, and contrast on the captured image based on the extracted irregularity information and the enhancement level (see FIG. 9).

This makes it possible to perform the enhancement process on the captured image (e.g., the entire captured image) without limiting the enhancement target to a specific protrusion. Specific examples of the enhancement level, and the advantageous effects achieved by this configuration are the same as described above in connection with the first embodiment. Therefore, detailed description thereof is omitted.

The enhancement level setting section 3335 may increase the enhancement level set to a protrusion included in the extracted irregularity information as the degree of agreement of the width and the height of the protrusion with the dimensional information increases.

This makes it possible to appropriately enhance the enhancement target, and efficiently improve visibility, for example.

The enhancement level setting section 3335 may increase the enhancement level set to a protrusion included in the extracted irregularity information as the width of the protrusion decreases.

This makes it possible to perform the enhancement process so that a protrusion having a small width is enhanced to a large extent. In particular, when observing a polyp or the like (i.e., protrusion) within an in vivo image, since the color of a polyp does not differ to a large extent from the color of other areas, it is likely that a small polyp is missed. It is possible to prevent a situation in which a polyp or the like is missed by increasing the enhancement level when the size of a polyp or the like is small. Note that whether or not to increase the enhancement level is determined based on the width of the protrusion that corresponds to the size of a polyp in the direction orthogonal to the optical axis of the imaging section on the assumption that the imaging section 200 (almost) perpendicularly faces the wall surface of tissue. A situation in which the wall surface of a lumen structure is almost parallel to the optical axis direction of the imaging section 200 may occur during screening. In such a case, since it is possible to easily observe a situation in which a polyp protrudes from the wall surface of tissue to some extent, it may be unnecessary to change the enhancement level based on the height of a protrusion. Note that the enhancement level may be changed using information about the height of a protrusion. It is likely that a small polyp is missed. However, a polyp that is too small may be noise. Even when a protrusion that is too small is a polyp or the like, it is considered that the degree of severity is low. Therefore, the enhancement level may be decreased when the width of the protrusion is small (see FIG. 23B).

4. Third Embodiment

The third embodiment is described below. In the third embodiment, the enhancement section 333 improve the visibility of an early lesion by increasing the contrast of an irregular area. Therefore, both information about a recess and information about protrusion are used as the extracted irregularity information. For example, the information illustrated in FIG. 7C is used as the extracted irregularity information. A recess and a protrusion are set to be the attention area based on the extracted irregularity information. The enhancement process is implemented by adding an irregularity information signal to the Y signal (image signal). This makes it possible to increase the contrast of a recess and a protrusion.

Note that the irregularity information need not necessarily be added to the image signal. The irregularity information may be subjected to a high-pass filtering process to extract a high-frequency component, and the extracted high-frequency component may be added to the image signal. This makes it possible to increase the contrast at the boundary between irregular parts.

The first to third embodiments to which the invention is applied, and the modifications thereof have been described above. Note that the invention is not limited to the first to third embodiments and the modifications thereof. Various modifications and variations may be made without departing from the scope of the invention. A plurality of elements described above in connection with the first to third embodiments and the modifications thereof may be appropriately combined to achieve various configurations. For example, an arbitrary element may be omitted from the elements described above in connection with the first to third embodiments and the modifications thereof. Some of the elements described above in connection with different embodiments or modifications thereof may be appropriately combined. Any term cited with a different term having a broader meaning or the same meaning at least once in the specification and the drawings can be replaced with the different term in any place in the specification and the drawings. Various modifications and applications are possible without materially departing from the novel teachings and advantages of the invention.

What is claimed is:

1. An image processing device comprising:
a processor comprising hardware, wherein the processor is configured to:
   acquire a captured image of an object, wherein the captured image is an image captured by an image sensor;
   acquire distance information based on a distance from the image sensor to the object when the image sensor captured the captured image;
   acquire extracted irregularity information from the acquired distance information, wherein the extracted irregularity information represents irregular parts extracted from the object; and
perform an enhancement process on an enhancement target, wherein the enhancement target is an irregular part among the irregular parts represented by the extracted irregularity information that agrees with characteristics specified by known characteristic information, and wherein the known characteristic information is information that represents known characteristics relating to a structure of the object,
wherein in performing the enhancement process, the processor is configured to:
   acquire dimensional information as the known characteristic information, wherein the dimensional information represents at least one of a width and a depth of a recess of the object that is determined to be the enhancement target;
   set an enhancement level of the enhancement process for the recess based on the dimensional information; and
   perform a process that corrects at least one of a color, luminance, and contrast on the captured image based on the extracted irregularity information and the enhancement level.

2. The image processing device according to claim 1, wherein the processor is configured to increase the enhancement level set to the recess included in the extracted irregularity information as a degree of agreement of the width and the depth of the recess with the dimensional information increases.

3. The image processing device according to claim 1, wherein the processor is configured to decrease the enhancement level set to the recess included in the extracted irregularity information as the depth of the recess decreases.

4. An image processing device comprising:
a processor comprising hardware, wherein the processor is configured to:
   acquire a captured image of an object, wherein the captured image is an image captured by an image sensor;
   acquire distance information based on a distance from the image sensor to the object when the image sensor captured the captured image;
   acquire extracted irregularity information from the acquired distance information, wherein the extracted irregularity information represents irregular parts extracted from the object; and
perform an enhancement process on an enhancement target, wherein the enhancement target is an irregular part among the irregular parts represented by the extracted irregularity information that agrees with characteristics specified by known characteristic information, and wherein the known characteristic information is information that represents known characteristics relating to a structure of the object, wherein in performing the enhancement process, the processor is configured to:
- acquire dimensional information as the known characteristic information, wherein the dimensional information represents at least one of a width and a height of a protrusion of the object that is determined to be the enhancement target;
- set an enhancement level of the enhancement process for the protrusion based on the dimensional information; and
- perform a process that corrects at least one of a color, luminance, and contrast on the captured image based on the extracted irregularity information and the enhancement level.

5. The image processing device according to claim 4, wherein the processor is configured to increase the enhancement level set to the protrusion included in the extracted irregularity information as a degree of agreement of the width and the height of the protrusion with the dimensional information increases.

6. The image processing device according to claim 4, wherein the processor is configured to increase the enhancement level set to the protrusion included in the extracted irregularity information as the width of the protrusion decreases.

7. The image processing device according to claim 1, wherein the processor is configured to receive the known characteristic information inputted through an input device.

8. The image processing device according to claim 1, wherein the image sensor is configured to capture a plurality of the captured image from a plurality of viewpoints, and wherein the processor is configured to:
- acquire the plurality of the captured image that respectively correspond to the plurality of viewpoints; and
- acquire the distance information based on parallax information obtained from the plurality of the captured image acquired.

9. An information storage device storing a program that causes a computer to perform steps of:
- acquiring a captured image of an object, wherein the captured image is an image captured by an image sensor;
- acquiring distance information based on a distance from the image sensor to the object when the image sensor captured the captured image;
- acquiring extracted irregularity information from the acquired distance information, wherein the extracted irregularity information represents irregular parts extracted from the object; and
- performing an enhancement process on an enhancement target, wherein the enhancement target is an irregular part among the irregular parts represented by the extracted irregularity information that agrees with characteristics specified by known characteristic information, and wherein the known characteristic information is information that represents known characteristics relating to a structure of the object, wherein performing the enhancement process comprises:
- acquiring dimensional information as the known characteristic information, wherein the dimensional information represents at least one of a width and a depth of a recess of the object that is determined to be the enhancement target;
- setting an enhancement level of the enhancement process for the recess based on the dimensional information; and
- performing a process that corrects at least one of a color, luminance, and contrast on the captured image based on the extracted irregularity information and the enhancement level.

10. An image processing method comprising:
- acquiring a captured image of an object, wherein the captured image is an image captured by an image sensor;
- acquiring distance information based on a distance from the image sensor to the object when the image sensor captured the captured image;
- acquiring extracted irregularity information from the acquired distance information, wherein the extracted irregularity information is information that represents irregular parts extracted from the object; and
- performing an enhancement process on an enhancement target, wherein the enhancement target is an irregular part among the irregular parts represented by the extracted irregularity information that agrees with characteristics specified by known characteristic information, and wherein the known characteristic information is information that represents known characteristics relating to a structure of the object, wherein performing the enhancement process comprises:
- acquiring dimensional information as the known characteristic information, wherein the dimensional information represents at least one of a width and a depth of a recess of the object that is determined to be the enhancement target;
- setting an enhancement level of the enhancement process for the recess based on the dimensional information; and
- performing a process that corrects at least one of a color, luminance, and contrast on the captured image based on the extracted irregularity information and the enhancement level.

11. An information storage device storing a program that causes a computer to perform steps of:
- acquiring a captured image of an object, wherein the captured image is an image captured by an image sensor;
- acquiring distance information based on a distance from the image sensor to the object when the image sensor captured the captured image;
- acquiring extracted irregularity information from the acquired distance information, wherein the extracted irregularity information represents irregular parts extracted from the object; and
- performing an enhancement process on an enhancement target, wherein the enhancement target is an irregular part among the irregular parts represented by the extracted irregularity information that agrees with characteristics specified by known characteristic information, and wherein the known characteristic information is information that represents known characteristics relating to a structure of the object, wherein performing the enhancement process comprises:
- acquiring dimensional information as the known characteristic information, wherein the dimensional information represents at least one of a width and a depth of a protrusion of the object that is determined to be the enhancement target;

setting an enhancement level of the enhancement process for the protrusion based on the dimensional information; and performing a process that corrects at least one of a color, luminance, and contrast on the captured image based on the extracted irregularity information and the enhancement level.

12. An image processing method comprising:

acquiring a captured image of an object, wherein the captured image is an image captured by an image sensor;

acquiring distance information based on a distance from the image sensor to the object when the image sensor captured the captured image;

acquiring extracted irregularity information from the acquired distance information, wherein the extracted irregularity information is information that represents irregular parts extracted from the object;

performing an enhancement process on an enhancement target, wherein the enhancement target is an irregular part among the irregular parts represented by the extracted irregularity information that agrees with characteristics specified by known characteristic information, and wherein the known characteristic information is information that represents known characteristics relating to a structure of the object;

wherein performing the enhancement process comprises:

acquiring dimensional information as the known characteristic information, wherein the dimensional information represents at least one of a width and a depth of a protrusion of the object that is determined to be the enhancement target;

setting an enhancement level of the enhancement process for the protrusion based on the dimensional information; and performing a process that corrects at least one of a color, luminance, and contrast on the captured image based on the extracted irregularity information and the enhancement level.

* * * * *